(12) United States Patent
Gagliardo et al.

(10) Patent No.: US 12,102,416 B2
(45) Date of Patent: Oct. 1, 2024

(54) USING DATA FROM A BODY WORN SENSOR TO MODIFY MONITORED PHYSIOLOGICAL DATA

(71) Applicant: Spacelabs Healthcare L.L.C., Snoqualmie, WA (US)

(72) Inventors: Richard Gagliardo, Sammamish, WA (US); Jeffrey Jay Gilham, Sammamish, WA (US); William Gregory Downs, Snoqualmie, WA (US)

(73) Assignee: Spacelabs Healthcare L.L.C., Snoqualmie, WA (US)

( * ) Notice: Subject to any disclaimer, the term of this patent is extended or adjusted under 35 U.S.C. 154(b) by 442 days.

(21) Appl. No.: 16/912,685

(22) Filed: Jun. 25, 2020

(65) Prior Publication Data
US 2020/0405156 A1 Dec. 31, 2020

Related U.S. Application Data

(60) Provisional application No. 62/866,621, filed on Jun. 26, 2019.

(51) Int. Cl.
*A61B 5/0205* (2006.01)
*A61B 5/00* (2006.01)
(Continued)

(52) U.S. Cl.
CPC ............. *A61B 5/0205* (2013.01); *A61B 5/11* (2013.01); *A61B 5/25* (2021.01); *A61B 5/6801* (2013.01);
(Continued)

(58) Field of Classification Search
CPC ........... A61B 5/0205; A61B 5/11; A61B 5/25; A61B 5/6801; A61B 2560/0214;
(Continued)

(56) References Cited

U.S. PATENT DOCUMENTS

| | | |
|---|---|---|
| 2,003,120 A | 5/1935 | William |
| 2,004,116 A | 6/1935 | Jennings |

(Continued)

FOREIGN PATENT DOCUMENTS

| | | |
|---|---|---|
| CN | 1293943 | 5/2001 |
| CN | 1293943 A | 5/2001 |

(Continued)

OTHER PUBLICATIONS

International Search Report for PCT/US2020/039705, Sep. 28, 2020.

(Continued)

*Primary Examiner* — Christopher A Flory

(74) *Attorney, Agent, or Firm* — Novel IP

(57) ABSTRACT

The present specification describes methods and systems for monitoring changes in physiological data, such as electrocardiogram data, respiration data, and blood pressure data, as a consequence of a change in position or movement of a subject under observation. Embodiments of the present specification provide systems for detecting and processing motion data by utilizing an available physiological monitoring device, with minimal additions of cost and equipment. A connecting wire is used to add a motion sensor to an existing physiological monitoring device. The connecting wire provides a channel for powering the motion sensing device as well as communication of data to and from the motion sensing device. Preferably, the motion sensor is embedded into the wire.

27 Claims, 12 Drawing Sheets

(51) Int. Cl.
*A61B 5/11* (2006.01)
*A61B 5/25* (2021.01)

(52) U.S. Cl.
CPC ............. *A61B 2560/0214* (2013.01); *A61B 2562/0219* (2013.01); *A61B 2562/166* (2013.01); *A61B 2562/227* (2013.01)

(58) Field of Classification Search
CPC ...... A61B 2562/0219; A61B 2562/166; A61B 2562/227
See application file for complete search history.

(56) References Cited

U.S. PATENT DOCUMENTS

| | | |
|---|---|---|
| 2,005,005 A | 6/1935 | Preston |
| 2,005,146 A | 6/1935 | Kotrbaty |
| 2,006,213 A | 6/1935 | Halliday |
| 2,007,120 A | 7/1935 | Holmes |
| 2,008,221 A | 7/1935 | Molander |
| 2,008,251 A | 7/1935 | Hillebrand |
| 2,009,121 A | 7/1935 | Price |
| 2,009,326 A | 7/1935 | Sanchez-Vello |
| 2,246,464 A | 6/1941 | Gerber |
| 2,808,580 A | 10/1957 | Fuller |
| 2,820,651 A | 1/1958 | Phillips |
| 2,912,858 A | 11/1959 | Fuller |
| 2,944,547 A | 7/1960 | Ziherl |
| 3,517,639 A | 6/1970 | Whitsel |
| 3,608,545 A | 9/1971 | Novack |
| 3,618,592 A | 11/1971 | Simpson |
| 3,673,863 A | 7/1972 | Spacek |
| 3,689,908 A | 9/1972 | Ray |
| 3,733,482 A | 5/1973 | Miller |
| 3,757,577 A | 9/1973 | Bozek |
| 3,844,171 A | 10/1974 | Rodger |
| 3,897,606 A | 8/1975 | Schleining |
| 3,938,551 A | 2/1976 | Henkin |
| 3,954,010 A | 5/1976 | Hilblom |
| 3,981,329 A | 9/1976 | Wohlwend |
| 4,064,826 A | 12/1977 | Pauli |
| 4,148,312 A | 4/1979 | Bird |
| 4,167,115 A | 9/1979 | Stoever |
| 4,323,064 A | 4/1982 | Hoenig |
| 4,365,331 A * | 12/1982 | Biba ................ H04L 12/2801 370/445 |
| 4,428,230 A | 1/1984 | Testone |
| 4,428,507 A | 1/1984 | Sneider |
| 4,513,294 A | 4/1985 | Anderson |
| 4,521,891 A * | 6/1985 | Biba ................ H04L 12/2801 375/222 |
| 4,557,216 A | 12/1985 | Demyon |
| 4,615,547 A | 10/1986 | Sutcliffe |
| 4,625,731 A | 12/1986 | Quedens |
| 4,630,485 A | 12/1986 | Wastlsr |
| 4,630,486 A | 12/1986 | Miles |
| 4,643,693 A | 2/1987 | Rubinstein |
| 4,697,450 A | 10/1987 | Bachman |
| 4,869,253 A | 9/1989 | Craig |
| 4,879,997 A | 11/1989 | Bickford |
| 4,899,585 A | 2/1990 | Kulha |
| 4,903,222 A | 2/1990 | Carter |
| 4,944,305 A | 7/1990 | Takatsu |
| 4,989,791 A | 2/1991 | Ridenour |
| 4,991,576 A | 2/1991 | Henkin |
| 4,993,683 A | 2/1991 | Kreuzer |
| 5,086,397 A | 2/1992 | Schuster |
| 5,087,906 A | 2/1992 | Eaton |
| 5,101,851 A | 4/1992 | Abadi |
| 5,144,898 A | 9/1992 | Posly |
| 5,174,163 A | 12/1992 | Gussman |
| 5,197,480 A | 3/1993 | Gebhardt |
| 5,213,108 A | 5/1993 | Bredesen |
| 5,222,486 A | 6/1993 | Vaughn |
| 5,231,981 A | 8/1993 | Schreiber |
| 5,233,975 A | 8/1993 | Choate |
| 5,253,641 A | 10/1993 | Choate |
| 5,262,944 A | 11/1993 | Weisner |
| 5,291,182 A | 3/1994 | Wiseman |
| 5,292,564 A | 3/1994 | Lee |
| 5,311,908 A | 5/1994 | Barone |
| 5,319,363 A | 6/1994 | Welch |
| 5,322,069 A | 6/1994 | Gallant |
| 5,331,549 A | 7/1994 | Crawford, Jr. |
| 5,333,106 A | 7/1994 | Lanpher |
| 5,339,826 A | 8/1994 | Schmidt |
| 5,348,008 A | 9/1994 | Bornn |
| 5,372,389 A | 12/1994 | Tam |
| 5,373,746 A | 12/1994 | Bloss |
| 5,375,604 A | 12/1994 | Kelly |
| 5,377,399 A | 1/1995 | Ogawa |
| 5,419,332 A | 5/1995 | Sabbah |
| 5,438,983 A | 8/1995 | Falcone |
| 5,467,954 A | 11/1995 | Wekell |
| 5,473,536 A | 12/1995 | Wimmer |
| 5,482,050 A | 1/1996 | Smokoff |
| 5,497,766 A | 3/1996 | Foster |
| 5,502,853 A | 4/1996 | Singleton |
| 5,515,083 A | 5/1996 | Casebolt |
| 5,520,191 A | 5/1996 | Karlsson |
| 5,537,992 A | 7/1996 | Bjoernstijerna |
| 5,553,296 A | 9/1996 | Forrest |
| 5,558,418 A | 9/1996 | Lambright |
| 5,558,638 A * | 9/1996 | Evers ................ A61B 5/0022 604/66 |
| 5,563,495 A | 10/1996 | Tomiyori |
| 5,584,291 A | 12/1996 | Vapola |
| 5,586,909 A | 12/1996 | Saba |
| 5,603,330 A | 2/1997 | Suga |
| 5,633,457 A | 5/1997 | Kilar |
| 5,682,526 A | 10/1997 | Smokoff |
| 5,684,504 A | 11/1997 | Verhulst |
| 5,687,717 A | 11/1997 | Halpern |
| 5,692,494 A | 12/1997 | Pernetti |
| 5,715,813 A | 2/1998 | Guevrekian |
| 5,718,235 A | 2/1998 | Golosarsky |
| 5,724,025 A | 3/1998 | Tavori |
| 5,724,985 A | 3/1998 | Snell |
| 5,749,367 A | 5/1998 | Gamlyn |
| 5,752,917 A | 5/1998 | Fuchs |
| 5,765,842 A | 6/1998 | Phaneuf |
| 5,779,305 A | 7/1998 | Hocking |
| 5,787,298 A | 7/1998 | Broedner |
| 5,800,360 A | 9/1998 | Kisner |
| 5,800,387 A | 9/1998 | Duffy |
| 5,819,741 A | 10/1998 | Karlsson |
| 5,852,440 A | 12/1998 | Grossman |
| 5,855,550 A | 1/1999 | Lai |
| 5,868,133 A | 2/1999 | Devries |
| 5,904,328 A | 5/1999 | Leveridge |
| 5,947,907 A | 9/1999 | Duich |
| 5,956,013 A | 9/1999 | Raj |
| 5,966,760 A | 10/1999 | Gallant |
| 5,975,081 A | 11/1999 | Hood |
| 6,005,767 A | 12/1999 | Ku |
| 6,008,809 A | 12/1999 | Brooks |
| 6,024,089 A | 2/2000 | Wallace |
| 6,042,548 A | 3/2000 | Giuffre |
| 6,048,044 A | 4/2000 | Biggel |
| 6,050,940 A | 4/2000 | Braun |
| 6,063,028 A | 5/2000 | Luciano |
| 6,096,025 A | 8/2000 | Borders |
| 6,099,093 A | 8/2000 | Spence |
| 6,115,643 A | 9/2000 | Stine |
| 6,131,571 A | 10/2000 | Lampotang |
| 6,134,537 A | 10/2000 | Pao |
| 6,146,523 A | 11/2000 | Kenley |
| 6,155,255 A | 12/2000 | Lambert |
| 6,167,401 A | 12/2000 | Csipkes |
| 6,188,407 B1 | 2/2001 | Smith |
| 6,221,012 B1 | 4/2001 | Maschke |
| 6,269,813 B1 | 8/2001 | Fitzgerald |
| 6,322,502 B1 | 11/2001 | Schoenberg |
| 6,338,823 B1 | 1/2002 | Furukawa |

(56) References Cited

U.S. PATENT DOCUMENTS

| | | | |
|---|---|---|---|
| 6,339,732 B1 | 1/2002 | Phoon | |
| 6,346,047 B1 * | 2/2002 | Sobota | A63F 13/235 |
| | | | 370/294 |
| 6,347,310 B1 | 2/2002 | Passera | |
| 6,349,436 B1 | 2/2002 | Kreuzer | |
| 6,364,834 B1 | 4/2002 | Reuss | |
| 6,383,136 B1 | 5/2002 | Jordan | |
| 6,396,583 B1 | 5/2002 | Clare | |
| 6,406,426 B1 | 6/2002 | Reuss | |
| 6,416,471 B1 | 7/2002 | Kumar | |
| 6,424,860 B1 | 7/2002 | Karlsson | |
| 6,435,690 B1 | 8/2002 | Till | |
| 6,443,889 B1 | 9/2002 | Groth | |
| D467,001 S | 12/2002 | Buczek | |
| 6,488,029 B1 | 12/2002 | Hood | |
| 6,536,430 B1 | 3/2003 | Smith | |
| 6,541,758 B2 | 4/2003 | Yashiro | |
| 6,554,238 B1 | 4/2003 | Hibberd | |
| 6,571,227 B1 | 5/2003 | Agrafiotis | |
| 6,571,792 B1 | 6/2003 | Hendrickson | |
| 6,591,694 B2 | 7/2003 | Tsai | |
| 6,600,662 B1 | 7/2003 | Emmert | |
| 6,605,046 B1 * | 8/2003 | Del Mar | A61B 5/282 |
| | | | 600/386 |
| 6,647,341 B1 | 11/2003 | Golub | |
| 6,650,779 B2 | 11/2003 | Vachtesvanos | |
| 6,674,837 B1 | 1/2004 | Taskar | |
| 6,692,258 B1 | 2/2004 | Kurzweil | |
| 6,692,436 B1 | 2/2004 | Bluth | |
| 6,699,187 B2 | 3/2004 | Webb | |
| 6,702,754 B2 | 3/2004 | Ogura | |
| 6,715,722 B2 | 4/2004 | Roberts | |
| 6,722,010 B2 | 4/2004 | Maruyama | |
| 6,725,184 B1 | 4/2004 | Gadh | |
| 6,735,648 B2 | 5/2004 | Onishi | |
| 6,771,172 B1 | 8/2004 | Robinson | |
| 6,790,178 B1 | 9/2004 | Mault | |
| 6,796,264 B1 | 9/2004 | Appenzeller | |
| 6,804,656 B1 | 10/2004 | Rosenfeld | |
| 6,824,539 B2 | 11/2004 | Novak | |
| 6,829,501 B2 | 12/2004 | Nielsen | |
| 6,868,495 B1 | 3/2005 | Glover | |
| 6,896,241 B2 | 5/2005 | Chen | |
| 6,931,795 B1 | 8/2005 | Baloga | |
| 6,933,931 B2 | 8/2005 | Lubarsky, Jr. | |
| 6,944,561 B2 | 9/2005 | Tseng | |
| 6,985,762 B2 | 1/2006 | Brashears | |
| 7,006,865 B1 | 2/2006 | Cohen | |
| 7,013,833 B2 | 3/2006 | Lemberger | |
| 7,024,569 B1 | 4/2006 | Wright | |
| 7,031,857 B2 | 4/2006 | Tarassenko | |
| 7,038,588 B2 | 5/2006 | Boone | |
| 7,040,175 B1 | 5/2006 | Huang | |
| 7,055,232 B2 | 6/2006 | Maruyama | |
| 7,076,435 B1 | 7/2006 | Mckeag | |
| 7,081,091 B2 | 7/2006 | Merrett | |
| RE39,233 E | 8/2006 | Mcgrath | |
| 7,096,864 B1 | 8/2006 | Mayer | |
| 7,111,852 B2 | 9/2006 | Woods | |
| 7,117,438 B2 | 10/2006 | Wallace | |
| 7,128,709 B2 | 10/2006 | Saruya | |
| 7,137,951 B2 | 11/2006 | Pilarski | |
| 7,193,233 B2 | 3/2007 | Smith | |
| 7,216,802 B1 | 5/2007 | De La Huerga | |
| 7,219,559 B2 | 5/2007 | Sugi | |
| 7,223,007 B1 | 5/2007 | Fredley | |
| 7,234,944 B2 | 6/2007 | Nordin | |
| 7,256,708 B2 | 8/2007 | Rosenfeld | |
| 7,265,676 B2 | 9/2007 | Gordon | |
| 7,267,666 B1 | 9/2007 | Duchon | |
| 7,282,029 B1 | 10/2007 | Poulsen | |
| 7,310,544 B2 | 12/2007 | Brister | |
| 7,315,825 B2 | 1/2008 | Rosenfeld | |
| 7,319,386 B2 | 1/2008 | Collins, Jr. | |
| 7,336,980 B1 | 2/2008 | Kaikuranta | |
| 7,360,454 B2 | 4/2008 | Kawashima | |
| 7,371,214 B2 | 5/2008 | Kouchi | |
| 7,386,340 B2 | 6/2008 | Schlegel | |
| 7,390,299 B2 | 6/2008 | Weiner | |
| 7,439,856 B2 | 10/2008 | Weiner | |
| 7,468,032 B2 | 12/2008 | Stahmann | |
| 7,469,601 B2 | 12/2008 | Sugi | |
| 7,489,250 B2 | 2/2009 | Bock | |
| D589,959 S | 4/2009 | Han | |
| 7,516,924 B2 | 4/2009 | White | |
| 7,523,040 B2 | 4/2009 | Kirchhoff | |
| 7,529,083 B2 | 5/2009 | Jeong | |
| 7,530,949 B2 | 5/2009 | Alali | |
| 7,540,187 B1 | 6/2009 | Dillon | |
| 7,556,039 B1 | 7/2009 | Peirry | |
| 7,566,307 B2 | 7/2009 | Inukai | |
| 7,621,500 B2 | 11/2009 | Ishizaki | |
| 7,704,212 B2 | 4/2010 | Wekell | |
| 7,710,567 B1 | 5/2010 | Mentzer | |
| 7,751,878 B1 | 7/2010 | Merkle | |
| 7,756,722 B2 | 7/2010 | Levine | |
| 7,831,670 B2 | 11/2010 | Goodman | |
| 7,836,882 B1 | 11/2010 | Rumph | |
| 7,945,452 B2 | 5/2011 | Fathallah | |
| 7,974,924 B2 | 7/2011 | Holla | |
| 8,002,701 B2 | 8/2011 | John | |
| 8,027,846 B2 | 9/2011 | Schoenberg | |
| 8,033,686 B2 | 10/2011 | Recker | |
| 8,091,422 B2 | 1/2012 | Felske | |
| 8,147,419 B2 | 4/2012 | Krauss | |
| 8,190,900 B2 | 5/2012 | Corndorf | |
| 8,233,272 B2 | 7/2012 | Fidacaro | |
| 8,273,018 B1 | 9/2012 | Fackler | |
| 8,344,847 B2 | 1/2013 | Moberg | |
| 8,398,408 B1 | 3/2013 | Hansen | |
| 8,413,271 B2 | 4/2013 | Blanchard | |
| 8,544,406 B2 | 10/2013 | Fujihira | |
| 8,593,275 B2 | 11/2013 | Davis | |
| 8,704,666 B2 | 4/2014 | Baker, Jr. | |
| 8,738,118 B2 * | 5/2014 | Moon | A61B 5/1116 |
| | | | 600/513 |
| 8,798,527 B2 | 8/2014 | Gaines | |
| 8,811,888 B2 | 8/2014 | Wiesner | |
| 8,818,260 B2 | 8/2014 | Gaines | |
| 8,855,550 B2 | 10/2014 | Gaines | |
| 8,868,028 B1 | 10/2014 | Kaltsukis | |
| 8,897,198 B2 | 11/2014 | Gaines | |
| 8,903,308 B2 | 12/2014 | Wiesner | |
| 8,922,330 B2 | 12/2014 | Moberg | |
| 8,931,702 B2 | 1/2015 | Wekell | |
| 8,940,147 B1 | 1/2015 | Bartsch | |
| 8,943,168 B2 | 1/2015 | Wiesner | |
| 9,020,419 B2 | 4/2015 | Gaines | |
| 9,086,313 B2 | 7/2015 | Tobia | |
| 9,844,637 B2 | 12/2017 | Beduhn | |
| 10,617,302 B2 * | 4/2020 | Al-Ali | A61B 5/0059 |
| 2001/0001179 A1 | 5/2001 | Healy | |
| 2001/0004234 A1 | 6/2001 | Petelenz | |
| 2001/0018332 A1 | 8/2001 | Lustila | |
| 2001/0027791 A1 | 10/2001 | Wallace | |
| 2001/0034475 A1 | 10/2001 | Flach | |
| 2002/0013517 A1 | 1/2002 | West | |
| 2002/0026941 A1 | 3/2002 | Biondi | |
| 2002/0032386 A1 | 3/2002 | Sackner | |
| 2002/0040954 A1 | 4/2002 | Roberts | |
| 2002/0060247 A1 | 5/2002 | Krishnaswamy | |
| 2002/0095424 A1 | 7/2002 | Chung | |
| 2002/0108011 A1 | 8/2002 | Tanha | |
| 2002/0138017 A1 | 9/2002 | Bui | |
| 2002/0161291 A1 | 10/2002 | Kianl | |
| 2002/0173991 A1 | 11/2002 | Avitall | |
| 2002/0193679 A1 | 12/2002 | Malave | |
| 2002/0196141 A1 | 12/2002 | Boone | |
| 2002/0196234 A1 | 12/2002 | Gray | |
| 2003/0028118 A1 | 2/2003 | Dupree | |
| 2003/0029451 A1 | 2/2003 | Blair | |
| 2003/0037786 A1 | 2/2003 | Biondi | |
| 2003/0065536 A1 | 4/2003 | Hansen | |
| 2003/0076015 A1 | 4/2003 | Ehrenreich | |

(56) References Cited

U.S. PATENT DOCUMENTS

| | | |
|---|---|---|
| 2003/0092974 A1 | 5/2003 | Santoso |
| 2003/0114836 A1 | 6/2003 | Estes |
| 2003/0117296 A1 | 6/2003 | Seely |
| 2003/0120164 A1 | 6/2003 | Nielsen |
| 2003/0130590 A1 | 7/2003 | Bui |
| 2003/0135087 A1 | 7/2003 | Hickle |
| 2003/0144699 A1 | 7/2003 | Freeman |
| 2003/0145854 A1 | 8/2003 | Hickle |
| 2003/0158492 A1 | 8/2003 | Sheldon |
| 2003/0171898 A1 | 9/2003 | Tarassenko |
| 2003/0191373 A1 | 10/2003 | Blike |
| 2003/0197614 A1 | 10/2003 | Smith |
| 2003/0209246 A1 | 11/2003 | Schroeder |
| 2003/0210780 A1 | 11/2003 | Pratt |
| 2003/0216621 A1 | 11/2003 | Alpert |
| 2003/0231460 A1 | 12/2003 | Moscovitch |
| 2003/0233129 A1 | 12/2003 | Matos |
| 2004/0008825 A1 | 1/2004 | Seeley |
| 2004/0011938 A1 | 1/2004 | Oddsen |
| 2004/0015079 A1 | 1/2004 | Berger |
| 2004/0021705 A1 | 2/2004 | Baker |
| 2004/0024303 A1 | 2/2004 | Banks |
| 2004/0032426 A1 | 2/2004 | Rutledge |
| 2004/0054261 A1 | 3/2004 | Kamataki |
| 2004/0054295 A1 | 3/2004 | Ramseth |
| 2004/0073128 A1 | 4/2004 | Hatlestad |
| 2004/0077954 A1 | 4/2004 | Oakley |
| 2004/0102687 A1 | 5/2004 | Brashears |
| 2004/0103001 A1 | 5/2004 | Mazar |
| 2004/0113895 A1 | 6/2004 | Andre |
| 2004/0116813 A1 | 6/2004 | Selzer |
| 2004/0117209 A1 | 6/2004 | Brown |
| 2004/0117233 A1 | 6/2004 | Rapp |
| 2004/0118404 A1 | 6/2004 | Wallace |
| 2004/0147818 A1 | 7/2004 | Levy |
| 2004/0149892 A1 | 8/2004 | Akitt |
| 2004/0153257 A1 | 8/2004 | Munk |
| 2004/0158132 A1 | 8/2004 | Zaleski |
| 2004/0172078 A1 | 9/2004 | Chinchoy |
| 2004/0172222 A1 | 9/2004 | Simpson |
| 2004/0186357 A1 | 9/2004 | Soderberg |
| 2004/0220629 A1 | 11/2004 | Kamath |
| 2004/0221077 A1 | 11/2004 | Yen |
| 2004/0236192 A1 | 11/2004 | Necolashehada |
| 2004/0240167 A1 | 12/2004 | Ledbetter |
| 2004/0249298 A1 | 12/2004 | Selevan |
| 2004/0249673 A1 | 12/2004 | Smith |
| 2005/0005932 A1 | 1/2005 | Berman |
| 2005/0010165 A1 | 1/2005 | Hickle |
| 2005/0033124 A1 | 2/2005 | Kelly |
| 2005/0033188 A1 | 2/2005 | Whitaker |
| 2005/0038332 A1 | 2/2005 | Saidara |
| 2005/0038821 A1 | 2/2005 | Wallen |
| 2005/0054920 A1 | 3/2005 | Washburn |
| 2005/0059924 A1 | 3/2005 | Katz |
| 2005/0065417 A1 | 3/2005 | Ali |
| 2005/0113650 A1 | 5/2005 | Pacione |
| 2005/0113704 A1 | 5/2005 | Lawson |
| 2005/0124866 A1 | 6/2005 | Elaz |
| 2005/0139213 A1 | 6/2005 | Blike |
| 2005/0146431 A1 | 7/2005 | Hastings |
| 2005/0148890 A1 | 7/2005 | Hastings |
| 2005/0151640 A1 | 7/2005 | Hastings |
| 2005/0177096 A1 | 8/2005 | Bollish |
| 2005/0192845 A1 | 9/2005 | Brinsfield |
| 2005/0193263 A1 | 9/2005 | Watt |
| 2005/0229110 A1 | 10/2005 | Gegner |
| 2005/0251232 A1 | 11/2005 | Hartley |
| 2006/0004475 A1 | 1/2006 | Brackett |
| 2006/0013462 A1 | 1/2006 | Sadikali |
| 2006/0022096 A1 | 2/2006 | Chan |
| 2006/0042635 A1 | 3/2006 | Niklewski |
| 2006/0053034 A1 | 3/2006 | Hlathein |
| 2006/0058591 A1 | 3/2006 | Garboski |
| 2006/0094970 A1 | 5/2006 | Drew |
| 2006/0142808 A1 | 6/2006 | Pearce |
| 2006/0155206 A1 | 7/2006 | Lynn |
| 2006/0155589 A1 | 7/2006 | Lane |
| 2006/0161295 A1 | 7/2006 | Yun |
| 2006/0199618 A1 | 9/2006 | Steer |
| 2006/0213517 A1 | 9/2006 | Mashak |
| 2006/0226992 A1 | 10/2006 | Al-Ali |
| 2006/0235316 A1* | 10/2006 | Ungless .................. A61B 5/11 600/509 |
| 2006/0252999 A1 | 11/2006 | Devaul |
| 2006/0258926 A1 | 11/2006 | Ali |
| 2006/0261781 A1 | 11/2006 | Oberding |
| 2006/0272141 A1 | 12/2006 | Rudduck |
| 2006/0278270 A1 | 12/2006 | Jones |
| 2006/0280621 A1 | 12/2006 | Kinugawa |
| 2006/0282021 A1 | 12/2006 | Devaul |
| 2006/0282302 A1 | 12/2006 | Hussain |
| 2006/0290525 A1 | 12/2006 | Andersen |
| 2007/0007418 A1 | 1/2007 | Lubbers |
| 2007/0028921 A1 | 2/2007 | Banner |
| 2007/0032749 A1 | 2/2007 | Overall |
| 2007/0044578 A1 | 3/2007 | Jones |
| 2007/0047797 A1 | 3/2007 | Vilella |
| 2007/0049127 A1 | 3/2007 | Nordin |
| 2007/0050715 A1 | 3/2007 | Behar |
| 2007/0051861 A1 | 3/2007 | Teramachi |
| 2007/0060869 A1 | 3/2007 | Tolle |
| 2007/0063850 A1 | 3/2007 | Devaul |
| 2007/0093784 A1 | 4/2007 | Leonard |
| 2007/0100213 A1 | 5/2007 | Dossas |
| 2007/0107728 A1 | 5/2007 | Ricciardelli |
| 2007/0108291 A1 | 5/2007 | Bhatia |
| 2007/0120763 A1 | 5/2007 | Depaepe |
| 2007/0136023 A1 | 6/2007 | Schoenborn |
| 2007/0165865 A1* | 7/2007 | Talvitie .................. H04L 63/123 380/286 |
| 2007/0176931 A1 | 8/2007 | Tivig |
| 2007/0180140 A1 | 8/2007 | Welch |
| 2007/0197881 A1 | 8/2007 | Wolf |
| 2007/0199388 A1 | 8/2007 | Furkert |
| 2007/0199566 A1 | 8/2007 | Be |
| 2007/0255116 A1 | 11/2007 | Mehta |
| 2007/0265533 A1 | 11/2007 | Tran |
| 2007/0276277 A1 | 11/2007 | Booth |
| 2007/0296571 A1 | 12/2007 | Kolen |
| 2008/0033254 A1 | 2/2008 | Kamath |
| 2008/0039701 A1 | 2/2008 | Ali |
| 2008/0039735 A1 | 2/2008 | Hickerson |
| 2008/0051667 A1 | 2/2008 | Goldreich |
| 2008/0077435 A1 | 3/2008 | Muradia |
| 2008/0103375 A1 | 5/2008 | Kiani |
| 2008/0117029 A1 | 5/2008 | Dohrmann |
| 2008/0154909 A1 | 6/2008 | Dam |
| 2008/0167569 A1 | 7/2008 | Ermes |
| 2008/0170287 A1 | 7/2008 | Champion |
| 2008/0177160 A1 | 7/2008 | Al Ali |
| 2008/0177397 A1 | 7/2008 | Davlin |
| 2008/0181465 A1 | 7/2008 | Sauerwein |
| 2008/0194918 A1 | 8/2008 | Kulik |
| 2008/0208381 A1 | 8/2008 | Soga |
| 2008/0221418 A1 | 9/2008 | Al-Ali |
| 2008/0221495 A1 | 9/2008 | Steffens |
| 2008/0228045 A1 | 9/2008 | Gao |
| 2008/0228089 A1 | 9/2008 | Cho |
| 2008/0249376 A1 | 10/2008 | Zaleski |
| 2008/0251003 A1 | 10/2008 | Boston |
| 2008/0267790 A1 | 10/2008 | Gaudet |
| 2008/0271736 A1 | 11/2008 | Leonard |
| 2008/0275309 A1 | 11/2008 | Stivoric |
| 2008/0281168 A1 | 11/2008 | Gibson |
| 2008/0281170 A1 | 11/2008 | Eshelman |
| 2008/0287763 A1 | 11/2008 | Hayter |
| 2008/0294057 A1 | 11/2008 | Parlikar |
| 2008/0310600 A1 | 12/2008 | Clawson |
| 2008/0312709 A1 | 12/2008 | Volpe |
| 2008/0319331 A1 | 12/2008 | Zizzo |
| 2009/0005651 A1 | 1/2009 | Ward |
| 2009/0005703 A1 | 1/2009 | Fasciano |
| 2009/0015116 A1 | 1/2009 | Arceta |

(56) References Cited

U.S. PATENT DOCUMENTS

| | | |
|---|---|---|
| 2009/0024008 A1 | 1/2009 | Brunner |
| 2009/0043171 A1 | 2/2009 | Rule |
| 2009/0054743 A1 | 2/2009 | Stewart |
| 2009/0055735 A1 | 2/2009 | Zaleski |
| 2009/0069642 A1 | 3/2009 | Gao |
| 2009/0076345 A1 | 3/2009 | Manicka |
| 2009/0076397 A1 | 3/2009 | Libbus |
| 2009/0099480 A1 | 4/2009 | Salgo |
| 2009/0117784 A1 | 5/2009 | Wu |
| 2009/0121592 A1 | 5/2009 | De Nando |
| 2009/0124239 A1 | 5/2009 | Tsuei |
| 2009/0131759 A1 | 5/2009 | Sims |
| 2009/0131805 A1 | 5/2009 | Obrien |
| 2009/0133609 A1 | 5/2009 | Nethken |
| 2009/0149901 A1 | 6/2009 | Jayne |
| 2009/0151720 A1 | 6/2009 | Inoue |
| 2009/0182204 A1 | 7/2009 | Semler |
| 2009/0190713 A1 | 7/2009 | Wai |
| 2009/0192541 A1 | 7/2009 | Ortiz |
| 2009/0193315 A1 | 7/2009 | Gower |
| 2009/0200902 A1 | 8/2009 | Mckay |
| 2009/0206713 A1 | 8/2009 | Vilkas |
| 2009/0209849 A1 | 8/2009 | Rowe |
| 2009/0213034 A1 | 8/2009 | Wu |
| 2009/0237264 A1 | 9/2009 | Bobey |
| 2009/0248173 A1 | 10/2009 | Sasko |
| 2009/0275805 A1 | 11/2009 | Lane |
| 2009/0292227 A1 | 11/2009 | Scholten |
| 2009/0326340 A1 | 12/2009 | Wang |
| 2010/0004539 A1 | 1/2010 | Chen |
| 2010/0007588 A1 | 1/2010 | Zygmunt |
| 2010/0014229 A1 | 1/2010 | Horie |
| 2010/0056875 A1 | 3/2010 | Schoenberg |
| 2010/0056877 A1 | 3/2010 | Fein |
| 2010/0070417 A1 | 3/2010 | Flynn |
| 2010/0073915 A1 | 3/2010 | Nittou |
| 2010/0094096 A1 | 4/2010 | Petruzzelli |
| 2010/0110019 A1 | 5/2010 | Ozias |
| 2010/0137729 A1 | 6/2010 | Pierry |
| 2010/0156655 A1 | 6/2010 | Bullemer |
| 2010/0164452 A1 | 7/2010 | Ruan |
| 2010/0175695 A1 | 7/2010 | Jamison |
| 2010/0179400 A1 | 7/2010 | Brauker |
| 2010/0198027 A1 | 8/2010 | Dixon |
| 2010/0233891 A1 | 9/2010 | Broeksteeg |
| 2010/0238138 A1 | 9/2010 | Goertz |
| 2010/0245091 A1 | 9/2010 | Singh |
| 2010/0259881 A1 | 10/2010 | Choi |
| 2010/0261979 A1 | 10/2010 | Kiani |
| 2010/0273530 A1 | 10/2010 | Jarvis |
| 2010/0282256 A1 | 11/2010 | Loescher |
| 2010/0285771 A1 | 11/2010 | Peabody |
| 2010/0294405 A1 | 11/2010 | Longinotti-Buitoni |
| 2010/0298654 A1* | 11/2010 | McCombie ............ A61B 5/282 |
| | | 600/595 |
| 2010/0298655 A1 | 11/2010 | Mccombie |
| 2010/0298656 A1 | 11/2010 | Mccombie |
| 2010/0298718 A1 | 11/2010 | Gilham |
| 2010/0318578 A1 | 12/2010 | Treu |
| 2010/0324380 A1 | 12/2010 | Perkins |
| 2010/0324384 A1 | 12/2010 | Moon |
| 2010/0324936 A1 | 12/2010 | Vishnubhatla |
| 2011/0004071 A1 | 1/2011 | Faiola |
| 2011/0006876 A1 | 1/2011 | Moberg |
| 2011/0015493 A1 | 1/2011 | Koschek |
| 2011/0054267 A1 | 3/2011 | Fidacaro |
| 2011/0055205 A1 | 3/2011 | Scott |
| 2011/0066045 A1 | 3/2011 | Moon |
| 2011/0066051 A1* | 3/2011 | Moon ............... A61B 5/02225 |
| | | 600/509 |
| 2011/0071420 A1 | 3/2011 | Pierre |
| 2011/0077971 A1 | 3/2011 | Surwit |
| 2011/0087756 A1 | 4/2011 | Biondi |
| 2011/0088694 A1 | 4/2011 | Tobia |
| 2011/0092780 A1 | 4/2011 | Zhang |
| 2011/0092838 A1 | 4/2011 | Helfenbein |
| 2011/0125040 A1 | 5/2011 | Crawford |
| 2011/0130798 A1 | 6/2011 | Elghazzawi |
| 2011/0138323 A1 | 6/2011 | Skidmore |
| 2011/0146676 A1 | 6/2011 | Dallam |
| 2011/0152629 A1 | 6/2011 | Eaton |
| 2011/0164074 A1 | 7/2011 | Frank |
| 2011/0190643 A1 | 8/2011 | Zhang |
| 2011/0224531 A1 | 9/2011 | Steiner |
| 2011/0225771 A1 | 9/2011 | Bartnick |
| 2011/0227739 A1 | 9/2011 | Gilham |
| 2011/0245579 A1 | 10/2011 | Bruggeman |
| 2011/0245688 A1 | 10/2011 | Arora |
| 2011/0257489 A1 | 10/2011 | Banet |
| 2011/0270058 A1 | 11/2011 | Price |
| 2011/0279383 A1 | 11/2011 | Wilson |
| 2011/0279958 A1 | 11/2011 | Clark |
| 2011/0295426 A1 | 12/2011 | Georgeson |
| 2011/0298718 A1 | 12/2011 | Chang |
| 2011/0301435 A1 | 12/2011 | Albert |
| 2012/0030610 A1 | 2/2012 | Diperna |
| 2012/0041783 A1 | 2/2012 | Mckee |
| 2012/0041786 A1 | 2/2012 | Yu |
| 2012/0075060 A1 | 3/2012 | Connor |
| 2012/0075327 A1 | 3/2012 | Mackenzie |
| 2012/0083906 A1 | 4/2012 | Weatherhead |
| 2012/0093311 A1 | 4/2012 | Nierzwick |
| 2012/0095778 A1 | 4/2012 | Gross |
| 2012/0101396 A1 | 4/2012 | Solosko |
| 2012/0101411 A1 | 4/2012 | Hausdorff |
| 2012/0105233 A1 | 5/2012 | Bobey |
| 2012/0105774 A1 | 5/2012 | Fletcher |
| 2012/0108991 A1 | 5/2012 | Song |
| 2012/0116331 A1 | 5/2012 | Locke |
| 2012/0127103 A1 | 5/2012 | Qualey |
| 2012/0136231 A1 | 5/2012 | Markel |
| 2012/0180789 A1 | 7/2012 | Tobia |
| 2012/0184120 A1 | 7/2012 | Basta |
| 2012/0186583 A1 | 7/2012 | Drapes |
| 2012/0203491 A1 | 8/2012 | Sun |
| 2012/0209984 A1 | 8/2012 | Gonzalez-Banos |
| 2012/0232398 A1 | 9/2012 | Roham |
| 2012/0233679 A1 | 9/2012 | Shedrinsky |
| 2012/0245439 A1 | 9/2012 | Andre |
| 2012/0265089 A1 | 10/2012 | Orr |
| 2012/0330675 A1 | 12/2012 | Muradia |
| 2013/0015966 A1 | 1/2013 | Soomro |
| 2013/0030258 A1 | 1/2013 | Cheung |
| 2013/0107445 A1 | 5/2013 | Reber |
| 2013/0116514 A1 | 5/2013 | Kroner |
| 2013/0162426 A1 | 6/2013 | Wiesner |
| 2013/0237772 A1 | 9/2013 | Pisani |
| 2013/0267861 A1 | 10/2013 | Vassallo |
| 2014/0142963 A1 | 5/2014 | Hill |
| 2014/0153747 A1 | 6/2014 | Contolini |
| 2014/0275873 A1 | 9/2014 | Fries |
| 2014/0275928 A1* | 9/2014 | Acquista ............... A61N 1/3987 |
| | | 600/382 |
| 2014/0337777 A1 | 11/2014 | Senesac |
| 2015/0018703 A1 | 1/2015 | Shetty |
| 2015/0374256 A1 | 12/2015 | Skrabal |
| 2016/0120445 A1 | 5/2016 | Peluso |
| 2016/0157718 A1 | 6/2016 | Barnes |
| 2016/0206224 A1* | 7/2016 | Marek ...................... A61B 5/11 |
| 2017/0215797 A1 | 8/2017 | Cretu-Petra |
| 2018/0271380 A1 | 9/2018 | Gregg |
| 2020/0289185 A1* | 9/2020 | Forsyth ............. A61B 18/1233 |
| 2020/0330037 A1* | 10/2020 | Al-Ali ................... F04B 53/001 |

FOREIGN PATENT DOCUMENTS

| | | |
|---|---|---|
| CN | 1348740 | 5/2002 |
| CN | 1518427 A | 8/2004 |
| CN | 1593764 A | 3/2005 |
| CN | 1688256 | 10/2005 |
| CN | 1781107 A | 5/2006 |
| CN | 1839311 A | 9/2006 |
| CN | 1943505 A | 4/2007 |
| CN | 1983258 A | 6/2007 |

(56) References Cited

FOREIGN PATENT DOCUMENTS

| | | |
|---|---|---|
| CN | 100391403 C | 6/2008 |
| CN | 101194278 | 6/2008 |
| CN | 101496923 | 8/2009 |
| CN | 101496923 A | 8/2009 |
| CN | 101501683 | 8/2009 |
| CN | 101521845 | 9/2009 |
| CN | 101521845 A | 9/2009 |
| CN | 101547716 A | 9/2009 |
| CN | 101611410 | 12/2009 |
| CN | 201570216 U | 9/2010 |
| CN | 201594642 U | 9/2010 |
| CN | 101893916 | 11/2010 |
| CN | 201708829 U | 1/2011 |
| CN | 102184312 | 9/2011 |
| CN | 102567624 | 7/2012 |
| CN | 203379114 U | 1/2014 |
| DE | 9415672 | 11/1994 |
| DE | 102006011151 | 9/2007 |
| EP | 0596509 A1 | 5/1994 |
| EP | 0686900 | 12/1995 |
| EP | 0686900 A2 | 12/1995 |
| EP | 0955007 A1 | 11/1999 |
| EP | 1054338 | 11/2000 |
| EP | 1227752 A1 | 5/2001 |
| EP | 1197178 A1 | 4/2002 |
| EP | 1406198 A2 | 4/2004 |
| EP | 1449558 | 8/2004 |
| EP | 1852060 | 11/2007 |
| EP | 1868123 A1 | 12/2007 |
| EP | 1197178 | 7/2008 |
| EP | 2555668 A2 | 2/2013 |
| EP | 2641151 | 9/2013 |
| EP | 2651482 | 10/2013 |
| EP | 2709518 | 3/2014 |
| EP | 2805564 A4 | 9/2015 |
| FR | 2908623 A1 * | 5/2008 ........... A61B 5/0002 |
| FR | 2908624 A1 * | 5/2008 ........... A61B 5/0002 |
| GB | 191214095 | 10/1912 |
| GB | 568212 | 3/1945 |
| GB | 2348715 | 10/2000 |
| GB | 2389290 A | 12/2003 |
| GB | 2438495 | 11/2007 |
| JP | 13286735 | 12/1991 |
| JP | 05143611 | 6/1993 |
| JP | 15184550 | 7/1993 |
| JP | 15341771 | 12/1993 |
| JP | 07163527 | 6/1995 |
| JP | H07227381 | 8/1995 |
| JP | 08504345 | 5/1996 |
| JP | 08504531 | 5/1996 |
| JP | 08275926 | 10/1996 |
| JP | 19108194 | 4/1997 |
| JP | 3059292 | 7/1999 |
| JP | 2001052281 | 2/2001 |
| JP | 2003210422 | 7/2003 |
| JP | 2003220039 | 8/2003 |
| JP | 2004147994 | 5/2004 |
| JP | 2004208855 | 7/2004 |
| JP | 2005529396 | 9/2005 |
| JP | 2008520026 | 6/2008 |
| JP | 2008532587 | 8/2008 |
| JP | 2009054381 | 3/2009 |
| JP | 2009517160 | 4/2009 |
| JP | 2009518153 | 5/2009 |
| JP | 2009211589 | 9/2009 |
| JP | 2009245435 | 10/2009 |
| JP | 2009544431 | 12/2009 |
| JP | 2010086535 | 4/2010 |
| JP | 2010533559 | 10/2010 |
| JP | 2011078640 | 4/2011 |
| JP | 2012529926 | 11/2012 |
| JP | 2018506338 | 3/2018 |
| WO | 9415523 A1 | 7/1994 |
| WO | 1994015523 | 7/1994 |
| WO | 1999018705 | 4/1999 |
| WO | 1999027326 | 6/1999 |
| WO | 2000042911 | 7/2000 |
| WO | 0134023 | 5/2001 |
| WO | 03091841 | 11/2003 |
| WO | 03102850 | 12/2003 |
| WO | 2004038669 A1 | 5/2004 |
| WO | 2004070994 A2 | 8/2004 |
| WO | 2005101276 A3 | 10/2005 |
| WO | 2005114524 A3 | 12/2005 |
| WO | 2006051464 A1 | 5/2006 |
| WO | 2006090371 | 8/2006 |
| WO | 2006094055 A2 | 9/2006 |
| WO | 2008005921 A1 | 1/2008 |
| WO | 2008079746 A2 | 7/2008 |
| WO | 2010126797 | 11/2010 |
| WO | 2010126797 A1 | 11/2010 |
| WO | 2010126916 | 11/2010 |
| WO | 2010126916 A1 | 11/2010 |
| WO | 2010144720 A1 | 12/2010 |
| WO | 2011001302 | 1/2011 |
| WO | 2011001302 A1 | 1/2011 |
| WO | 2011046636 A1 | 4/2011 |
| WO | 2011047363 A1 | 4/2011 |
| WO | 2011119512 A1 | 9/2011 |
| WO | 2012068564 A2 | 5/2012 |
| WO | 2012068565 A2 | 5/2012 |
| WO | 2012068567 | 5/2012 |
| WO | 2012068568 A2 | 5/2012 |
| WO | 2012083276 A2 | 6/2012 |
| WO | 2012083281 A1 | 6/2012 |
| WO | 2012125135 A1 | 9/2012 |
| WO | 2012128808 A2 | 9/2012 |
| WO | 2012158720 A1 | 11/2012 |
| WO | 2013056171 A2 | 4/2013 |
| WO | 2013173520 A2 | 11/2013 |
| WO | 2013173521 A2 | 11/2013 |
| WO | 2014055660 A1 | 4/2014 |
| WO | 2014194193 | 12/2014 |

OTHER PUBLICATIONS

International Preliminary Report on Patentability for PCT/US2020/039705, Dec. 28, 2021.
"BleaseSirius Anesthesia Systems User Manual 1073-0212-00/REV. B", Dec. 1, 2010, pp. 1-258, XP055209666.
"Lifegard II Patient Monitor Operator's Manual", Jan. 1, 2006, pp. 1-1, XP055209485.
Google patents search, Sep. 25, 2015, U.S. Appl. No. 14/044,524.
IntelliVue Patient Monitor; MP20/30, MP40/50, MP60/70/80/90, Release G.0 with Software Revision G.0x.xx (PHILIPS) Sep. 2008; pp. 4, 10, 19, 20, 46-49, 82, 326, 348, 420, 422, 424, 452; Accessed on Sep. 30, 2013: <http://www.mc.vanderbilt.edu/documents/nursingeducationresources/files/MP20-MP90%20Instructions%20for%20Use%20Manual%20Rev_G_0%20%20English%20M8000-9001K.pdf>.
International Preliminary Report on Patentability, PCT/US12/38000, Nov. 13, 2013.
International Preliminary Report on Patentability, PCT/US2006/007269, Sep. 11, 2007, Spacelabs Medical.
International Preliminary Report on Patentability, PCT/US2011/028007, Sep. 17, 2013, International Search Authority.
International Preliminary Report on Patentability, PCT/US2011/065678, Jun. 18, 2013, International Search Authority.
International Preliminary Report on Patentability, PCT/US2011/065685, Jun. 18, 2013.
International Preliminary Report on Patentability for PCT/US2011/061554, Feb. 25, 2014.
International Search Report, PCT/US2011/028007, Jul. 11, 2011, International Search Authority.
International Search Report, PCT/US2011/065685, May 8, 2012, International Search Authority.
International Search Report for PCT/US06/07269, Aug. 28, 2006.
International Search Report for PCT/US10/32635, Jul. 23, 2010.
International Search Report for PCT/US10/34025, Aug. 9, 2010.
International Search Report for PCT/US12/38000, Oct. 23, 2012.

(56) References Cited

OTHER PUBLICATIONS

International Search Report for PCT/US2010/052977, Mar. 18, 2011.
International Search Report for PCT/US2011/029278, Aug. 2, 2011.
International Search Report for PCT/US2011/061554, Feb. 14, 2014.
International Search Report for PCT/US2011/061555, Apr. 17, 2012.
International Search Report for PCT/US2011/061558, Aug. 10, 2012.
International Search Report for PCT/US2011/065676, Sep. 20, 2012.
International Search Report for PCT/US2011/065678, Jun. 29, 2012.
International Search Report for PCT/US2011/61557, Apr. 23, 2012.
International Search Report for PCT/US2012/060125, Apr. 19, 2013.
International Search Report for PCT/US2013/041246, Dec. 9, 2013.
International Search Report for PCT/US2013/041247, Jan. 10, 2014.
International Search Report for PCT/US2013/063087, Mar. 6, 2014.
International Search Report for PCT/US2014/040225, Nov. 5, 2014.
Schoenberg, Roy, MD; Sands, Daniel Z., MD MPH; Safran, Charles, MD; Center for Clinical Computing, Beth Israel Deaconess Medical Center, Harvard Medical School, "Making ICU Alarms Meaningful: a comparison of traditional vs. trend-based algorithms" (AMIA '99 Annual Symposium), 1999, pp. 1-5.
Google patents search, Apr. 9, 2018.
Philips: 'IntelliVue Patient Monitor; MP20/30, MP40/50, MP60/70/80/90', Internet Citation, Sep. 1, 2008, pp. 2PP, I-X, 1, XP003034216.
Anonymous: 'Docking station-wikipedia, the free encyclopedia', Feb. 20, 2012, XP055284610.
Anonymous: 'Pogo pin-wikipedia, the free encyclopedia', Apr. 28, 2012, XP055284974.
Anonymous: "Routing table", Wikipedia, Oct. 3, 2012 (Oct. 3, 2012), XP055321398, Retrieved from the Internet: URL: https://en.wikipedia.org/w/index.php?title=Routing_table&oldid=515747820, [retrieved on Nov. 21, 2016].
Anonymous: "Metrics (networking)", Wikipedia, Jul. 18, 2012 (Jul. 18, 2012), XP055321558, Retrieved from the Internet: URL: https://en.wikipedia.org/w/index.php?title=Metrics_(networking)&oldid=502970743, [retrieved on Nov. 22, 2016].
GE Healthcare, Modular monitoring for critical care, iMM Solar 8000i and iMM Transport Pro Monitors, 2005.
GE Healthcare, Carescape Monitor B850, Engineered to help provide better care, 2009.
Anonymous: "Framebuffer—Wikipedia, the free encyclopedia", Mar. 14, 2010, XP055307861, Retrieved from the Internet: URL—https://en.wikipedia.org/w/index.php?title=Framebuffer&oldid=349748376 [retrieved on Oct. 5, 2016].
"IntelliVue Patient Monitor MP20/30, MP40/50, MP60/70/80/90 Release G.0 with Software Revision G.0X.XX" Sep. 2008; See particularly pp. 3-19.
Kevin James: "Status Checks", PC Interfacing and Data Acquisition: Techniques for Measurement, Instrumentation and Control, Jul. 17, 2000, pp. 66-67, XP055461225, ISBN:978-0-7506-4624-6.
*Aerotel Ltd* v *Telco Holdings Ltd* Ord Rev 1 [2007] RPC 7 (Aerotel/Macrossam).
*Symbian* v *Comptroller General of Patents* [2008] EWCA Civ 1066.
*AT&T Knowledge Ventures LP* and *Cvon Innovations Ltd* v *Comptroller General of patents* [2009] EWHX 343 (Pat).
*HTC Europe Co Ltd* v *Apple linc* [2013] EWCA Civ 451.
*Lantana* v *Comptroller—General of Patents* [2013] EWHC 2673 (Pat).
Written Opinion of the International Searching Authority for PCT/US11/28007, Jul. 11, 2011.

\* cited by examiner

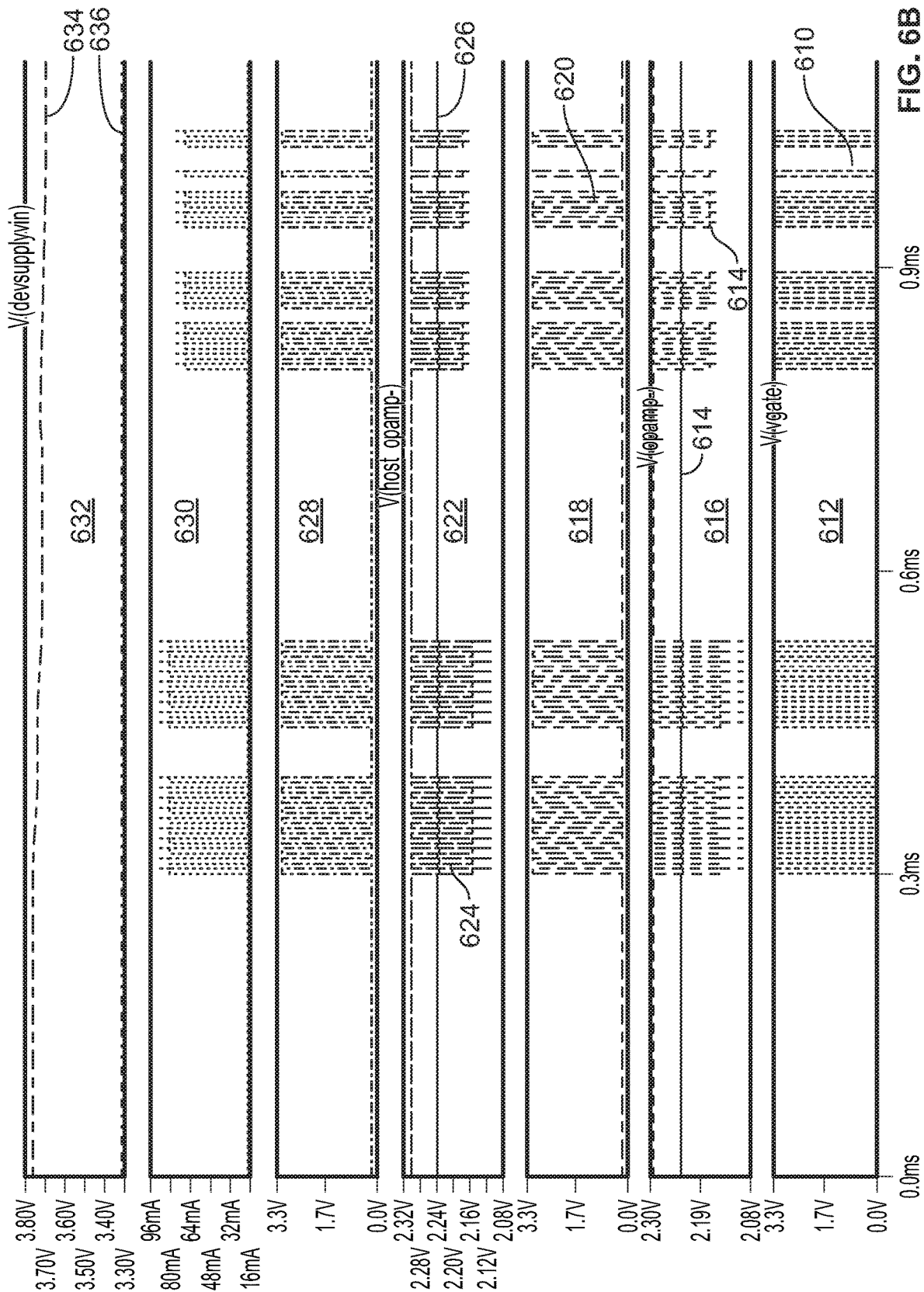

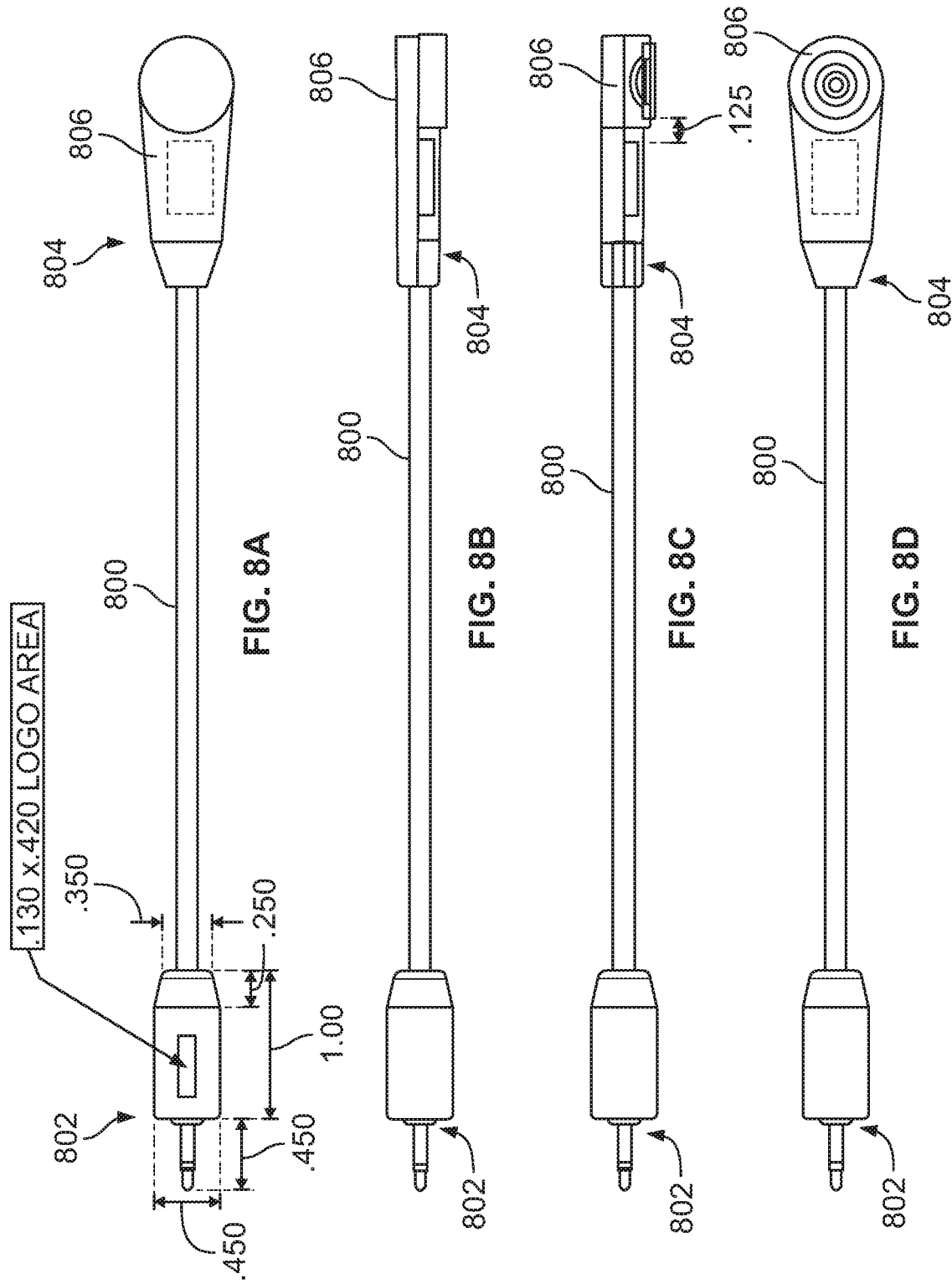

USING DATA FROM A BODY WORN SENSOR TO MODIFY MONITORED PHYSIOLOGICAL DATA

CROSS-REFERENCE

The present application relies on U.S. Patent Provisional Application No. 62/866,621, entitled "Using Data From a Body Worn Sensor to Modify Monitored Physiological Data", and filed on Jun. 26, 2019, for priority.

FIELD

The present specification relates generally to monitoring health-related parameters and more specifically to methods and systems for mounting sensors, such as a motion sensor, on the body of a person and using the sensors to provide activity and relative positional information about the person in order to correct, adjust, or otherwise modify physiological data. Additionally, the present specification relates to using a single-wire communication system for integrating the motion sensor with at least one other sensor.

BACKGROUND

Most monitors measure irregular heart-beats or any other irregular or abnormal physiological activity. An ambulatory electrocardiogram (AECG), which is consistently worn anywhere between 24 hours to a week or more, monitors electrocardiogram (ECG) data. Similarly, blood pressure (BP) monitors are used for hypertension management and cardiac monitoring. The monitors generate alarms, which may indicate an, or varying levels of, emergency in response to detection of an abnormal condition. However, often there are cases when a sensor detects what appears to be abnormal physiological activity due to a change in the patient's position or due to the patient's movement, yet the patient is actually healthy and his or her health status does not warrant an alarm. This may be especially true for ambulatory patients. For example, a person using a BP monitor may be exercising when the BP levels are detected as being abnormal. Similarly, an AECG monitor may falsely raise an alarm when the heart-beat of a wearer appears to be abnormal during exercising.

Even though exercise may skew physiological monitoring, low acuity patients need to be active to speed their recovery. Therefore, it may be desirable to be able to monitor their movements over a period of time. Some monitors combine information about different types of physiological data to conclude whether a wearer of the monitor(s) (or patient) is experiencing an abnormal health condition. For example, several models of BP monitors from various manufacturers have been developed with an added function of irregular heartbeat detection. However, these monitors are also prone to providing false positives when an otherwise healthy person is in motion. In addition to exercising, false positives may also be generated due to other external events, such as any other type of physical stress for example while lifting an object, work, fatigue, and changes in environmental conditions. Sometimes, even changing posture while sleeping may generate a false positive.

There is therefore a need to combine motion detection information, such as through motion sensors, to be able to effectively monitor physiological data and reduce or eliminate false positives generated by physiological monitors. There is also a need to correlate motion and/or positional information of a patient with any other physiological data, which may be monitored continuously, regularly, or in real time, so as to enhance the reliability and accuracy of physiological data monitors and improve diagnosis. Current physiological monitoring systems, such as AECG monitors, are unable to effectively integrate motion detection information. The monitoring systems fail to effectively combine a motion detector within existing components without having to introduce circuit-level changes or other forms of system-related modifications. Therefore, there is a need for a simple method and system that may be seamlessly integrated with existing monitoring systems, to add the capability of motion detection. It is also desirable to combine motion detection information with the physiological monitoring information to provide users with correlated data.

Many communication methods exist where one electronic device can communicate to another or several other devices over multiple wires. Communication methods are also needed to combine motion sensor data with devices for other purposes, in order to minimize the cost and apparatus needed for the combination. For some designs, however, it becomes more practical to minimize the number of wires necessary for communication. Devices are known to use a single-wire bus for bi-directional communication. The single wire connection used for bi-directional communication can interconnect two or more devices. A master device is known to be connected to one or more slave devices for communication of data and for slave device(s) to draw power from the master device. A system is needed that enables efficient, low-cost, and reliable communication between a motion detecting device and any other physiological monitoring device.

SUMMARY

The following embodiments and aspects thereof are described and illustrated in conjunction with systems, tools and methods, which are meant to be exemplary and illustrative, not limiting in scope.

The present specification discloses a physiological lead wire configured to monitor a motion of a person and to monitor a physiological parameter of the person, comprising: a connecting wire having a first end and an opposing second end; a connector plug attached to the first end, wherein the connector plug is configured to electrically connect the physiological lead wire with a physiological monitoring system; a receptacle at the second end, wherein the receptacle is configured to attach to the person; a motion detector integrated into the receptacle, wherein the motion detector is configured to acquire positional and movement information of the person and transmit the positional and movement information over the connecting wire; and a physiological sensor integrated into the receptacle, wherein the physiological sensor is configured to acquire physiological data of the person and transmit the physiological data over the connecting wire and wherein the physiological data comprises at least one of ECG data, respiration data, $SpO_2$ data, or blood pressure data.

Optionally, the connecting wire is further adapted to channel power to the motion detector and to transmit data to and from the motion detector.

Optionally, the physiological sensor comprises an electrode configured to detect electrical signals generated by the person's cardiac activity. The electrode may be partially exposed outside the receptacle. The electrode may be configured to transmit the electrical signals generated by the person's cardiac activity through the connecting wire. Optionally, the electrode is positioned adjacent the motion detector and the motion detector comprises a printed circuit board having a power converter, a processor, a comparator and at least one of a three-axis accelerometer, a combination of a three-axis accelerometer and a gyroscope, or a combination of a three-axis accelerometer, a gyroscope, and a magnetometer integrated therein.

The present specification also discloses an electrocardiogram monitoring system configured to monitor a motion of a person and to monitor electrical signals generated by the person's heart, comprising: a monitoring device configured to receive data indicative of the electrical signals and data indicative of the motion of the person, wherein the monitoring device comprises at least two ports; a first electrocardiogram lead wire having a first end with a connector configured to connect to either of the at least two ports and having a second end with a receptacle, wherein the receptacle is configured to attach to the person and wherein the receptacle comprises an electrode and does not comprise a motion detector; and a second electrocardiogram lead wire having a first end with a connector configured to connect to either of the at least two ports and having a second end with a receptacle, wherein the receptacle is configured to attach to the person, wherein the receptacle comprises an electrode and a motion detector, and wherein the motion detector is configured to acquire positional and movement information of the person and transmit the positional and movement information over the second electrocardiogram lead wire.

Optionally, the second electrocardiogram lead wire is further adapted to channel power to the motion detector and to transmit data to and from the motion detector.

Optionally, in the first electrocardiogram lead wire, the electrode is partially exposed through the receptacle, is configured to detect the electrical signals, and is in electrical communication with the first electrocardiogram lead wire and, in the second electrocardiogram lead wire, the electrode is partially exposed through the receptacle, is configured to detect the electrical signals, and is in electrical communication with the first electrocardiogram lead wire.

Optionally, in the second electrocardiogram lead wire, the electrode is positioned adjacent the motion detector and the motion detector comprises a printed circuit board having a power converter, a processor, a comparator and at least one of a three-axis accelerometer, a combination of a three-axis accelerometer and a gyroscope, or a combination of a three-axis accelerometer, a gyroscope, and a magnetometer integrated therein.

Optionally, the monitoring device comprises a third port. Optionally, the electrocardiogram monitoring system further comprises a third electrocardiogram lead wire having a first end with a connector configured to connect to either of the at least two ports or the third port and having a second end with a receptacle, wherein the receptacle is configured to attach to the person and wherein the receptacle comprises an electrode and does not comprise a motion detector. Optionally, the monitoring device comprises a fourth port. Optionally, the electrocardiogram monitoring system further comprises a fourth electrocardiogram lead wire having a first end with a connector configured to connect to either of the at least two ports, the third port or the fourth port and having a second end with a receptacle, wherein the receptacle is configured to attach to the person and wherein the receptacle comprises an electrode and does not comprise a motion detector. Each of the at least two ports, the third port and the fourth port may be structurally equivalent and configured to receive a same shaped connector.

The present specification also discloses a respiration monitoring system configured to monitor a motion of a person and to monitor electrical signals generated by the person's respiration, comprising: a monitoring device configured to receive data indicative of the electrical signals and data indicative of the motion of the person, wherein the monitoring device comprises at least two ports; a first wire having a first end with a connector configured to connect to either of the at least two ports and having a second end with a receptacle, wherein the receptacle is configured to attach to the person and wherein the receptacle comprises a respiratory sensor and does not comprise a motion detector; and a second wire having a first end with a connector configured to connect to either of the at least two ports and having a second end with a receptacle, wherein the receptacle is configured to attach to the person, wherein the receptacle comprises a respiratory sensor and a motion detector, and wherein the motion detector is configured to acquire positional and movement information of the person and transmit the positional and movement information over the second wire.

Optionally, the second wire is further adapted to channel power to the motion detector and to transmit data to and from the motion detector.

The present specification also discloses an oxygen saturation monitoring system configured to monitor a motion of a person and to monitor electrical signals generated by the person's oxygen saturation, comprising: a monitoring device configured to receive data indicative of the electrical signals and data indicative of the motion of the person, wherein the monitoring device comprises at least two ports; a first wire having a first end with a connector configured to connect to either of the at least two ports and having a second end with a receptacle, wherein the receptacle is configured to attach to the person and wherein the receptacle comprises a blood oxygenation sensor and does not comprise a motion detector; and a second wire having a first end with a connector configured to connect to either of the at least two ports and having a second end with a receptacle, wherein the receptacle is configured to attach to the person, wherein the receptacle comprises a blood oxygenation sensor and a motion detector, and wherein the motion detector is configured to acquire positional and movement information of the person and transmit the positional and movement information over the second wire.

Optionally, the second wire is further adapted to channel power to the motion detector and to transmit data to and from the motion detector.

The present specification also discloses a method for monitoring a motion of a person and electrical signals generated by the person's heart, comprising: acquiring a monitoring device configured to receive data indicative of the electrical signals and data indicative of the motion of the person, wherein the monitoring device comprises at least two ports; connecting a first electrocardiogram lead wire to either of the at least two ports, wherein the first electrocardiogram lead wire comprises a first end with a connector configured to connect to either of the at least two ports and a second end with a receptacle, wherein the receptacle is configured to attach to the person and wherein the receptacle comprises an electrode and does not comprise a motion detector; attaching the electrode of first electrocardiogram lead wire to the person; connecting a second electrocardiogram lead wire to either of the at least two ports, wherein the second electrocardiogram lead wire has a first end with a connector configured to connect to either of the at least two ports and a second end with a receptacle, wherein the receptacle is configured to attach to the person, wherein the receptacle comprises an electrode and a motion detector, and wherein the motion detector is configured to acquire positional and movement information of the person and transmit the positional and movement information over the second electrocardiogram lead wire; attaching the electrode of second electrocardiogram lead wire to the person; activating the monitoring device; and recording data indicative of the electrical signals and data indicative of the motion of the person.

Optionally, the second electrocardiogram lead wire is further adapted to channel power to the motion detector and to transmit data to and from the motion detector.

Optionally, in the second electrocardiogram lead wire, the electrode is positioned adjacent the motion detector and wherein the motion detector comprises a printed circuit board having a power converter, a processor, a comparator and at least one of a three-axis accelerometer, a combination of a three-axis accelerometer and a gyroscope, or a combination of a three-axis accelerometer, a gyroscope, and a magnetometer integrated therein.

Optionally, the method further comprises connecting a third electrocardiogram lead wire to either of the at least two ports or a third port, wherein the third electrocardiogram lead wire has a first end with a connector configured to connect to either of the at least two ports or the third port and a second end with a receptacle, wherein the receptacle is configured to attach to the person, wherein the receptacle comprises an electrode and does not comprise a motion detector and attaching the electrode of the third electrocardiogram lead wire to the person. Optionally, the method further comprises connecting a fourth electrocardiogram lead wire to either of the at least two ports, the third port, or a fourth port, wherein the fourth electrocardiogram lead wire has a first end with a connector configured to connect to either of the at least two ports, the third port or the fourth port, and a second end with a receptacle, wherein the receptacle is configured to attach to the person, wherein the receptacle comprises an electrode and does not comprise a motion detector and attaching the electrode of the fourth electrocardiogram lead wire to the person. Each of the at least two ports, the third port and the fourth port may be structurally equivalent and configured to receive a same shaped connector.

The present specification also discloses a physiological monitoring system for monitoring a wearer of the system, comprising: at least one connecting wire, wherein each connecting wire comprises: a plug at a first end of the connecting wire; a receptacle at a second end of the connecting wire, wherein the first end is opposite to the second end of the connecting wire; and a motion sensor system in proximity to the receptacle, wherein the motion sensor system senses positional and movement information of the wearer and sends the information over the connecting wire; wherein the connecting wire provides a channel for power to power the motion sensor system and data communication to and from the motion sensor system.

Optionally, the plug comprises an interface to connect with a power source.

Optionally, the plug comprises an interface to connect with a data storage and processing system.

Optionally, the receptacle is a snap-connector receptacle that attaches with a body of the wearer.

Optionally, the receptacle attaches to a body of the wearer similarly to an Electrocardiogram (ECG) lead snap. The plug may interface with a physiological monitoring device. The physiological monitoring device may be an ECG monitoring device.

Optionally, the motion sensor system comprises: at least one motion sensor to detect the positional and movement information; and a processor to receive and process the detected information. The motion sensor may comprise at least one of a three-axis accelerometer; a combination of a three-axis accelerometer and a gyroscope; and a combination of a three-axis accelerometer, a gyroscope, and a magnetometer. The motion sensor may comprise an inclination detector. The motion sensor may be configured to provide movement indications in all directions. The motion sensor may be configured to provide angle indications in two axes.

Optionally, the motion sensor system communicates data to and from at least one other physiological monitoring device. The at least one other physiological monitoring device may be an ECG monitoring device, a respiration monitoring device, a blood pressure (BP) monitoring device, or a combination of two or more of an ECG monitoring device, a respiration monitoring device, and a blood pressure (BP) monitoring device.

The present specification also discloses a physiological monitoring system for monitoring a wearer of the system, comprising: at least one connecting wire, wherein each connecting wire comprises: a plug at a first end of the connecting wire; a receptacle at a second end of the connecting wire, wherein the first end is opposite to the second end of the connecting wire; and a motion sensor system in proximity to the receptacle, wherein the motion sensor system senses positional and movement information of the wearer and sends the information over the connecting wire; wherein the connecting wire provides a channel for power to power the motion sensor system and data communication to and from the motion sensor system.

Optionally, the plug comprises an interface to connect with a power source. Optionally, the plug comprises an interface to connect with a data storage and processing system.

Optionally, the receptacle is a snap-connector receptacle that attaches with a body of the wearer. Optionally, the receptacle attaches to a body of the wearer similarly to an Electrocardiogram (ECG) lead snap.

Optionally, the plug interfaces with a physiological monitoring device. The physiological monitoring device may be an ECG monitoring device.

Optionally, the motion sensor system comprises: at least one motion sensor to detect the positional and movement information; and a processor to receive and process the detected information. The motion sensor may comprise at least one of a three-axis accelerometer; a combination of a three-axis accelerometer and a gyroscope; and a combination of a three-axis accelerometer, a gyroscope, and a magnetometer. The motion sensor may comprise an inclination detector. The motion sensor may be configured to provide movement indications in all directions.

The motion sensor may be configured to provide angle indications in two axes.

Optionally, the motion sensor system communicates data to and from at least one other physiological monitoring device. The at least one other physiological monitoring device may be an ECG monitoring device, a respiration monitoring device, a blood pressure (BP) monitoring device, or a combination of two or more of an ECG monitoring device, a respiration monitoring device, and a blood pressure (BP) monitoring device.

The present specification also discloses a physiological monitoring system for monitoring a wearer of the system, comprising: at least one connecting wire, wherein each connecting wire comprises: a plug at a first end of the connecting wire, wherein the plug is configured to interface with a receptacle on the physiological monitoring system; a housing at a second end of the connecting wire, wherein the first end is opposite to the second end of the connecting wire; and a motion sensor system in the housing, wherein the motion sensor system senses positional and movement information of the wearer and sends the information over the connecting wire, wherein the motion sensor system comprises a power converter for converting power from the power source. The connecting wire provides a channel to transmit power from a power source in the physiological monitoring system to the motion sensor system and communicate positional and movement information from the motion sensor system.

Optionally, the receptacle on the physiological monitoring system is one of a plurality of receptacles. A shape of the receptacle may be different from the rest of the plurality of receptacles, or may be same as the rest of the plurality of receptacles.

The aforementioned and other embodiments of the present specification shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein:

FIG. 6B illustrates a sample of data transmission from the second device to the first device using the simulation circuit of FIG. 5, in accordance with some embodiments of the present specification;

FIG. 8A illustrates a top view of a receptacle portion of a wire, in accordance with some embodiments of the present specification;

FIG. 8B illustrates a side view of the receptacle portion of the wire, shown in FIG. 8A;

FIG. 8C illustrates a cross-sectional side view of the receptacle portion of the wire, shown in FIG. 8A; and FIG. 8D illustrates a bottom view of the receptacle portion of the wire, shown in FIG. 8A.

DETAILED DESCRIPTION

Figure 1A:
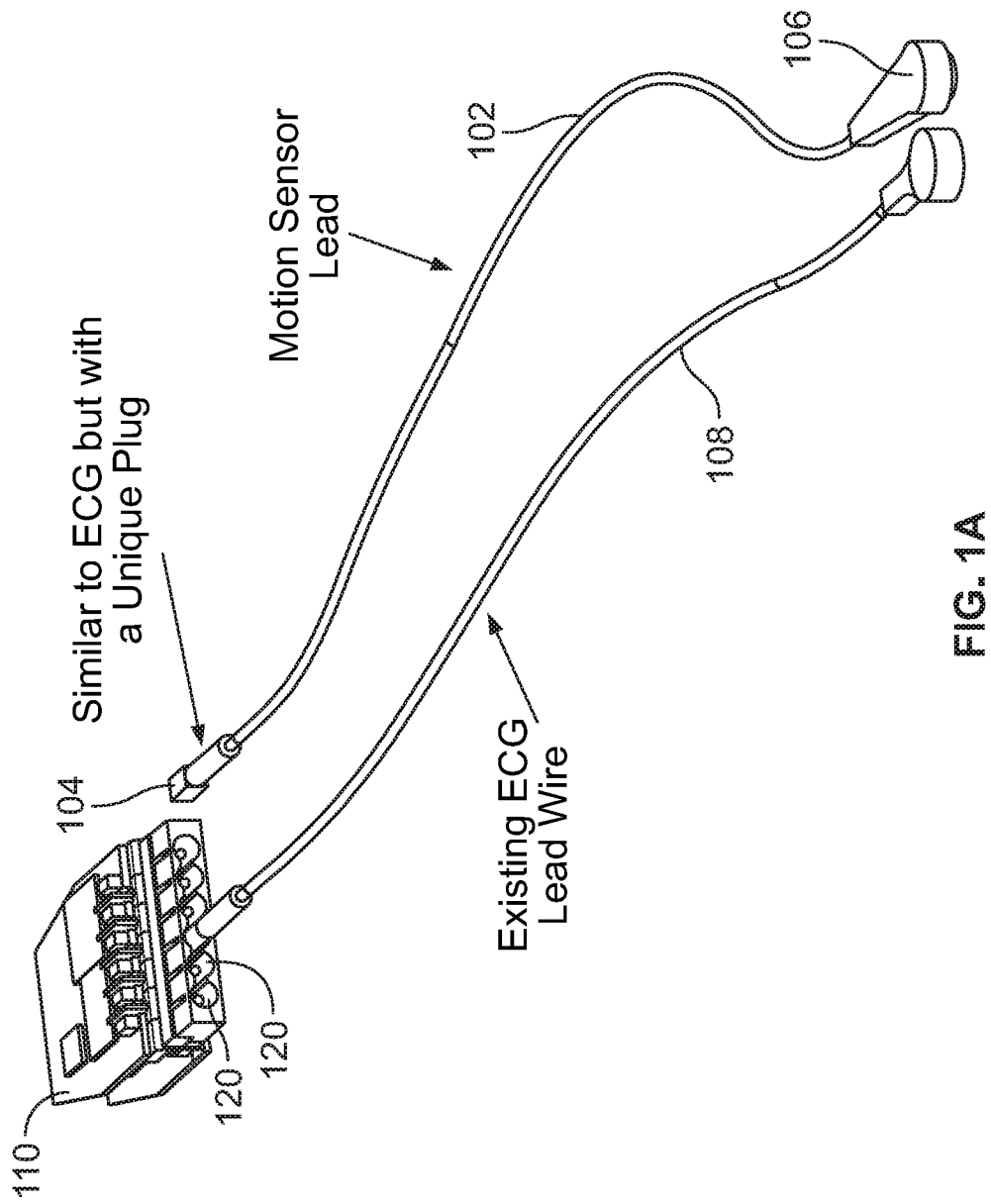
FIG. 1A illustrates a connecting wire comprising a motion sensor, in accordance with some embodiments of the present specification.
Figure 1B:
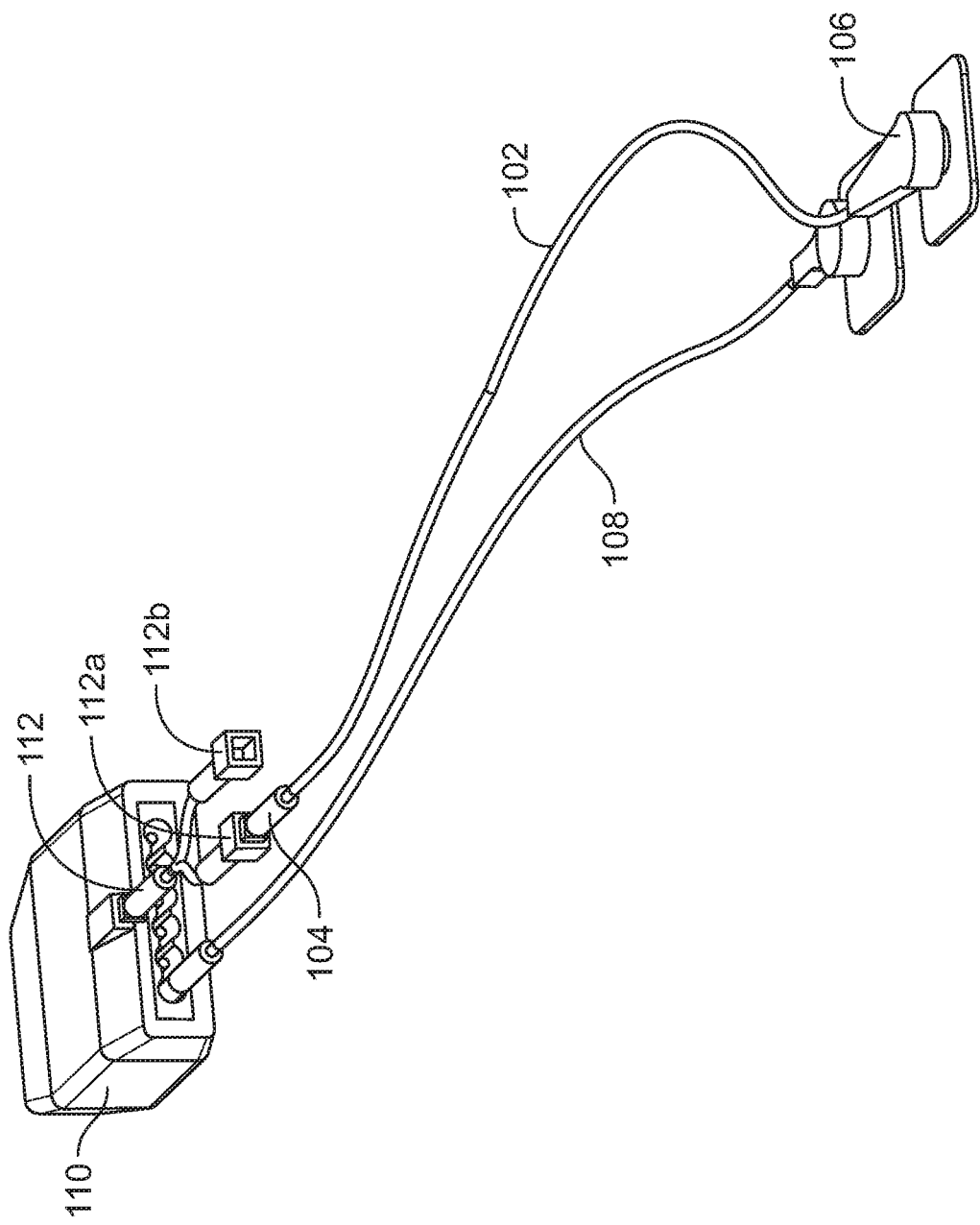
FIG. 1B illustrates an adapter cable to connect a connecting wire of FIG. 1A, in accordance with some embodiments of the present specification.
Figure 1C:
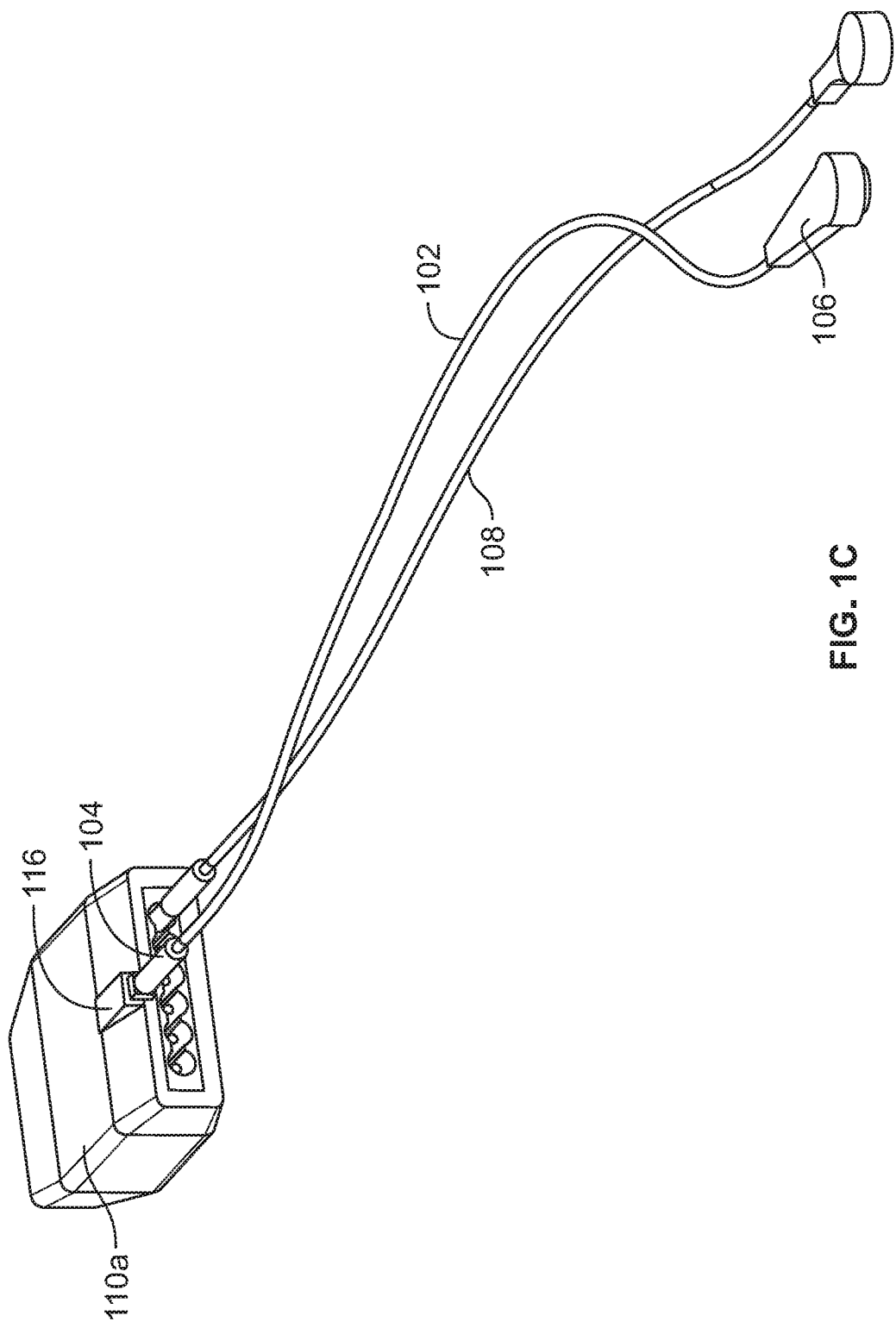
FIG. 1C illustrates an alternative embodiment of a physiological monitoring device comprising a separate connector for interfacing a motion sensing system, in accordance with some embodiments of the present specification.

In various embodiments, the present specification provides methods and systems to seamlessly integrate a motion detection system with existing physiological monitoring system. The motion detection system monitors changes in position and/or movement of a wearer of the physiological monitoring system. The monitored changes may be correlated with other physiological monitoring data to identify physiological abnormalities and aid in improving diagnosis. A single wire communication system enables interfacing between the position and/or movement sensing device and an existing or conventional physiological monitor.

Embodiments of the present specification provide a motion sensor system that can be embedded within a connecting wire that has the form and structure of an ECG lead wire. The connecting wire is compatible with a monitoring device, such as an ECG monitoring device. The connecting wire is connected similar to and in addition to other ECG lead wires that measure cardiac signals, to a physiological monitoring device. The connecting wire is used for providing power to the motion sensor system, which is integrated into the distal body of the ECG lead wire, and supporting bi-directional communication between the motion sensor system and the monitoring device. In alternative embodiments, the connecting wire with motion sensor system is compatible with any other physiological monitoring device, in addition to an ECG monitoring device. In embodiments, the motion sensor information is combined with information from one or more other physiological sensors to identify abnormalities and improve diagnosis.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

Embodiments of the present specification provide a connecting wire capable of connecting to a physiological monitoring device, such as an ECG monitor, also termed herein as ECG device or ECG monitoring device. Embodiments of the connecting wire are described below with respect to FIGS. 4, 5, 6A, and 6B. In an embodiment, the ECG device is a system that senses and analyses ECG signals by recording electrical activity of the heart. The monitoring is performed over a period of time using electrodes that are placed on the skin of a subject/person, such as a patient or other individual. In embodiments, the person is a patient or any other living being that is under observation for monitoring by the systems of the present specification. The ECG device typically interfaces with the electrodes through a connecting lead wire (ECG lead wire). The lead wire comprises an attachment mechanism at one end (proximal) for connection to the electrode(s) that are positioned on the subject's skin. The opposite end (distal) of the lead wire comprises a plug that interfaces with the ECG device. The heart muscle's electrophysiological pattern of depolarizing and repolarizing is measured and viewed in the form of a graph of voltage versus time (electrocardiogram). The electrocardiogram can be viewed on a screen attached to the ECG device, and/or can be printed on paper.

Ambulatory ECG devices use a small monitoring device worn by the subject which transmits monitored data from the device to a distant monitoring station using wireless communication. The device itself records, analyses, and communicates ECG data. Hardware components in the device enable sensing and storage, while software elements enable processing of data.

Sometimes hemodynamic monitoring is performed simultaneously with cardiac monitoring. Hemodynamic monitoring is usually performed using hydraulic circuits that monitor properties of blood flow. Some monitors combine respiration monitoring with ECG monitoring and/or hemodynamic monitoring, or just blood pressure (BP) monitoring. Respiration monitoring devices indicate respiration data like respiration rate, amplitude, and other characteristics. Most of these and other physiological monitoring devices receive the data concerning their objective, but also tend to receive noise that may arise due to motion of the subject. The motion data, when combined with other physiological monitoring data provides crucial diagnostic information about the subject.

Embodiments of the present specification can be configured to interface with an ECG device, a respiration monitoring device, a BP monitoring device, any other physiological monitoring device, or a combination of two or more of these devices. For instance, embodiments could be used on a patient who is wearing a Non-Invasive BP (NIBP) cuff or an $SpO_2$ sensor. The motion information derived from embodiments of the present specification would be used to provide more context to the collected NIBP or $SpO_2$ data, such as whether the patient is sitting up or active at the time of the reading. While some embodiments of systems of the present specification are described in the context of an ECG device (as the systems attach similarly to ECG electrodes and can be attached to a monitor in the same manner as an ECG lead wire, such as through a combiner (Yoke) cable or directly to the monitor), the systems of the present specification do not rely on any of the ECG components to operate. Embodiments of the present specification provide a low cost, portable option to additionally monitor position and movement-related data of a subject over a single wire for power and data, and combine the motion data with the other physiological data, in order to improve medical diagnosis as well as determine health or fitness levels.

FIG. 1A illustrates a connecting wire 102 comprising a motion sensing system, in accordance with some embodiments of the present specification. Wire 102 has two opposing ends including a connector/plug 104 at a first (distal) end and a receptacle 106 at a second (proximal) end. In one implementation, plug 104 is similar to the plug of an ECG lead wire 108 and therefore compatible with a conventional ECG monitor. Additionally, plug 104 can interface with a device 110. In one embodiment device 110 is an ECG device, and plug 104 connects to the ECG device similarly to the manner in which an ECG lead wire 108 interfaces with device 110. Accordingly, the present invention is directed toward a lead wire having a connector at one end that is compatible with a connection port of a conventional ECG monitoring device, a connection port of a conventional respiration monitoring device, a connection port of a conventional $SpO_2$ monitoring device, or a connection port of a conventional BP monitoring device such that the connector is structurally similar to a connector of a conventional ECG lead wire, a connector of a conventional respiration sensor, a connector of a conventional $SpO_2$ sensor, or a connector of a conventional blood pressure cuff, none of which have a motion sensor integrated therein.

The electrocardiogram monitoring system of FIG. 1A, according to embodiments of the present specification is configured to monitor a motion of a person and to monitor electrical signals generated by the person's heart. The ECG monitoring device 110 receives data indicative of the electrical signals from one or more ECG lead wires, including but not limited to lead wire 108 and motion sensor lead 102. Additionally, the motion sensor lead 102 provides data indicative of the motion of the person. Device 110 includes multiple ports 120 where at least one of the ports is used to connect to the motion sensor lead 102. The receptacle 106, positioned at the second (proximal) end of the motion sensor lead 102, attaches to the patient and includes an electrode and a motion detector to acquire positional and movement information of the patient and transmit the information over the motion sensor lead 102. One or more of the other remaining ports 120 on device 110 connect to one or more lead wires 108, which do not include a motion detector.

In one implementation receptacle 106 is configured similar to a snap-attach receptacle of ECG lead wire 108. A snap connector, also known as a pinch clip connector, may be attached to the body of a subject. The subject could be a patient, or any other being who is a wearer of the monitoring system and is to be monitored by the various embodiments of the present specification. Receptacle 106 may use the ECG adhesive snaps as a way to attach to the patient's body. In embodiments, the position or placement of receptacle 106 on the patient's body is independent of the placement of any ECG electrode. In some embodiments, optimal locations for placement of receptacle 106 are suggested to the patient, which allow for better detection of respiration activity (used to verify respiratory data or to signal breathing difficulty or stress).

In one embodiment, ECG adhesive pads are used to attach receptacle 106 to the subject. In various embodiments, receptacle 106 is configured in a manner similar to any type of an ECG electrode connector, such as but not limited to a wire dumbbell connector, a locking slot connector, or a keyhole connector. In embodiments, at least one motion sensor system is embedded in proximity to receptacle 106, and preferably within the housing of the receptacle 106. In one embodiment, a housing at the second end of wire 102 a motion sensor positioned within the receptacle 106. Connecting wire 102 is uniquely configured to communicate motion detection data from receptacle 106 to plug 104, which may be further recorded and/or processed by separate circuits within device 110. Connecting wire 102 provides a single path for powering the motion sensing device in receptacle 106 and enabling bi-directional communication between the motion sensing system and device 110. In embodiments, the data collected through the motion sensor system is correlated with data from an ECG monitor and/or other physiological monitoring systems, such as respiration data and blood pressure (BP) data.

In an embodiment, an adapter cable is used to connect multiple motion sensor systems to a physiological monitoring system, such as device 110 shown in FIG. 1. A plug portion of the adapter is configured to connect to a specific device 110 and may include any safety feature or unique/specialized aspect required to allow plug 104 to connect with wire 102. Multiple receptacles are electrically coupled to device 110 through the adapter cable, plug 104, and wire 102. FIG. 1B illustrates an adapter cable 112 used to connect multiple wires to device 110 of FIG. 1, in accordance with some embodiments of the present specification. Plug 104 connects to a connector 112a of adapter 112, while another connector portion 112b of adapter 112 is available to connect another wire, such as another motion sensor system. Additionally, FIG. 1C illustrates an alternative embodiment of a device 110a that includes a separate connector 116 to connect plug 104. Connector 116 may be provided in addition to the conventional connectors for interfacing with physiological monitoring device 110a. Connector 106 may also interface with an adapter 112 to connect with multiple sensors. Accordingly, connector comprises a first connector portion 112 configured to connect to a connector port of a conventional ECG monitoring device, a connection port of a conventional respiration monitoring device, or a connection port of a conventional BP monitoring device, a wire extending therefrom and being split into two or more prongs, where each prong leads to a port (112a, 112b, etc.) configured to receive a connector portion of an ECG lead wire, a cable of a respiration sensor, or a cable of a blood pressure cuff. It should be appreciated that while FIG. 1A shows a two-pronged connection, there could be 3, 4, 5, 6, 7, 8, 9, 10, or 100 prongs, or any whole number increment therein.

Figure 1D:
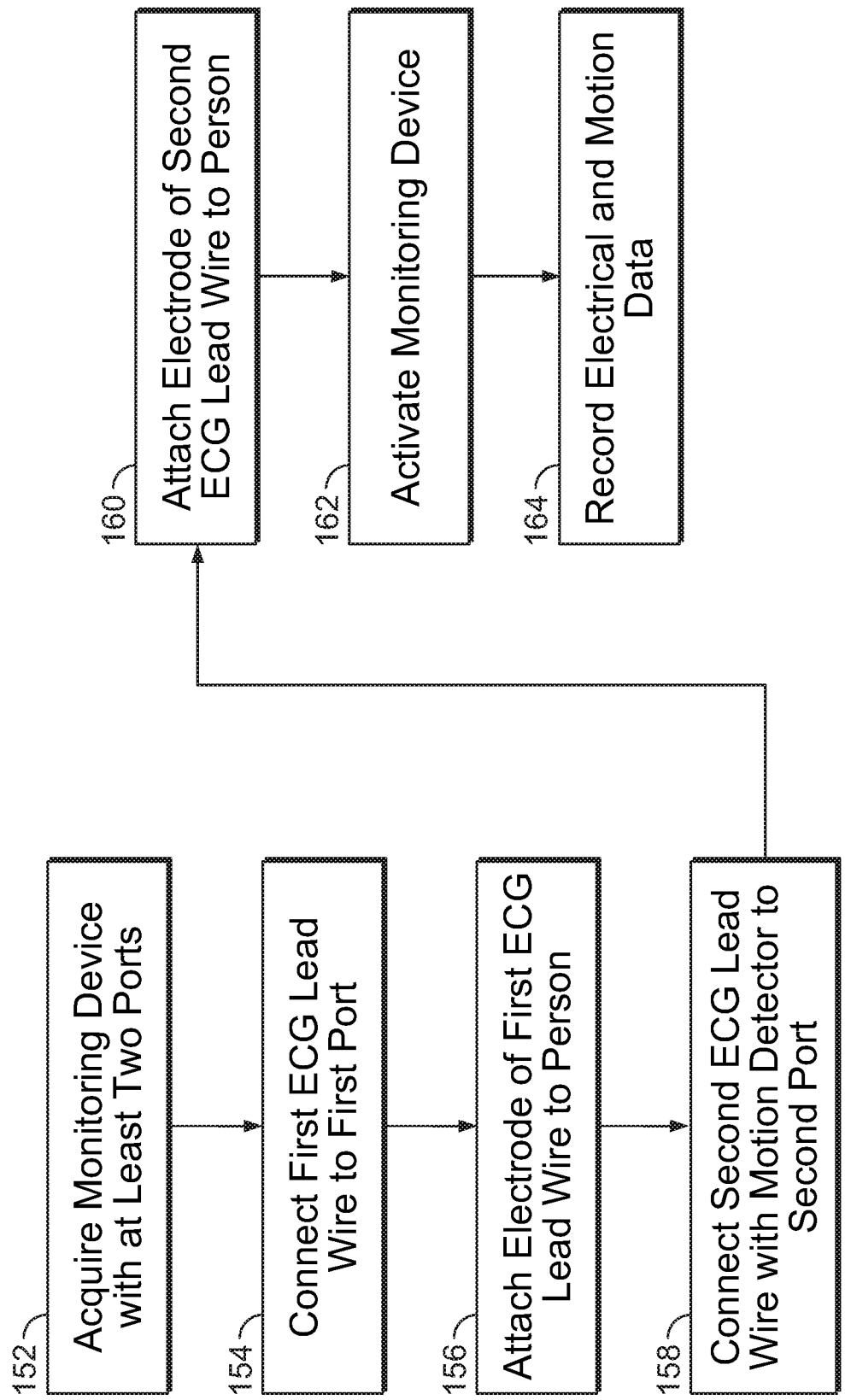
FIG. 1D is a flow chart showing steps for an exemplary process for monitoring both a motion of a person and electrical signals generated by the person's heart, in accordance with some embodiments of the present specification.

FIG. 1D is a flowchart showing exemplary process steps for monitoring both a motion of a person and electrical signals generated by the person's heart, in accordance with some embodiments of the present specification. The person is a patient or any other living being that is under observation for monitoring by the systems of the present specification. With reference to both FIGS. 1A and 1D, at step 152, the person, a physician or any other care provider for the person, acquires a monitoring device, such as device 110, configured to receive data indicative of the electrical signals and data indicative of the motion of the person. The monitoring device 110 includes two or more ports 120 that are used to connect ECG lead wires such as lead wire 108, which does not include a motion detector, and wire 102 which includes a motion detector, in their respective receptacles. Each of the two or more ports 120 of device 110 are structurally equivalent and are configured to receive a same shaped connector. At step 154, a first ECG lead wire, such as wire 108, is connected to a first port. In embodiments, wire 108 does not include a motion detector. The first port can be any one of the two or more ports 120 on device 110. A first end of the wire 108 includes a connector configured to connect to the port of device 110. A second end of the wire 108 includes a receptacle configured to attach to the person. The receptacle includes an electrode and does not comprise a motion detector. At step 156, the electrode of first ECG lead wire is attached to the person at a suitable location on the body of the person. At step 158, a second ECG lead wire, such as wire 102, is connected to a second port of the two or more ports 120 on device 110. The second ECG lead wire has a first end with a connector, such as plug 104, configured to the corresponding port on device 110. A second end of the wire 102 has a receptacle, such as receptacle 106, which includes an electrode and a motion detector, configured to attach to the person. The motion detector is configured to acquire positional and movement information of the person and transmit the positional and movement information over the second ECG lead wire (wire 102) to the monitoring device 110 when it is activated. Once device 110 is activated, wire 102 channels power to the motion detector and to transmit data to and from the motion detector. At step 160, the electrode of second ECG lead wire is attached to the person in a manner similar to any other ECG lead wire, such as wire 108. In some embodiments, a third ECG lead wire is attached to the device 110 at third port of the two or more ports 120. The third ECG lead wire is similar to the first ECG lead wire 108, and does not include a motion detector. A receptacle of the third wire is attached to the person similar to the first wire 108. In some embodiments, a fourth ECG lead wire is attached to the device 110 at yet another one of its ports. The fourth ECG lead wire is similar to the first ECG lead wire 108 and the third wire, and does not include a motion detector. A receptacle of the fourth wire is attached to the person similar to the first wire 108. At step 162, the monitoring device 110 is activated. The monitoring device 110 is activated by enabling power supply to operate the device 110, and optionally by selecting one or more options through a user interface such as buttons, to activate the device 110. At step 164, the monitoring device 110 records data indicative of the electrical signals and data indicative of the motion of the person.

The conventional physiological monitoring devices record and analyze data pertaining to their intended physiological parameter. Integration of real-time physiological data with position and/or movement-related data can be more effective in determining changes in the physiology of the subject. Physiological data can be monitored as a result of change in posture or movement of the subject.

Figure 2:
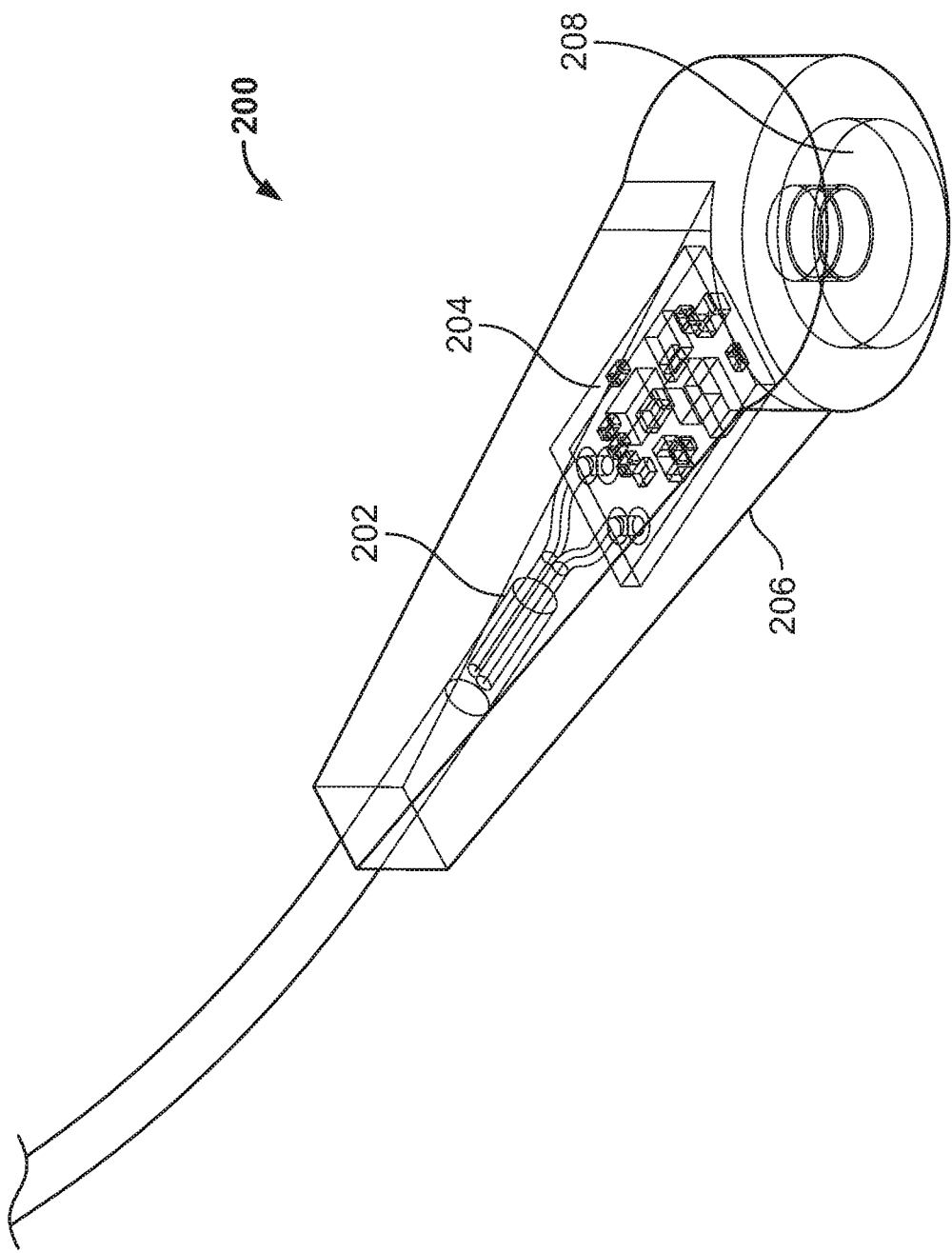
FIG. 2 illustrates an orthographic view of a receptacle shown in FIG. 1, in accordance with some embodiments of the present specification.

FIG. 2 illustrates an orthographic view of a receptacle 200 shown in FIG. 1, in accordance with some embodiments of the present specification. Receptacle 200 includes a housing 206 that encompasses components of an integrated motion sensor system 204. A lead connector 208 is located at the distal end of a connecting wire 202 within a portion of the housing 206 that interfaces with an electrode connector, analogous to an ECG electrode connector for the purpose of attaching receptacle 200 to the body of the subject. Motion sensor system 204 may comprise multiple components placed on a printed circuit board (PCB), and including elements that detect and process position and movement-related data. Accordingly, in one embodiment, the present invention is directed to a ECG electrode having a housing, an electrode embedded into, and exposed outside of, the housing, and a motion detector integrated into the housing, proximate the electrode.

Figure 3A:
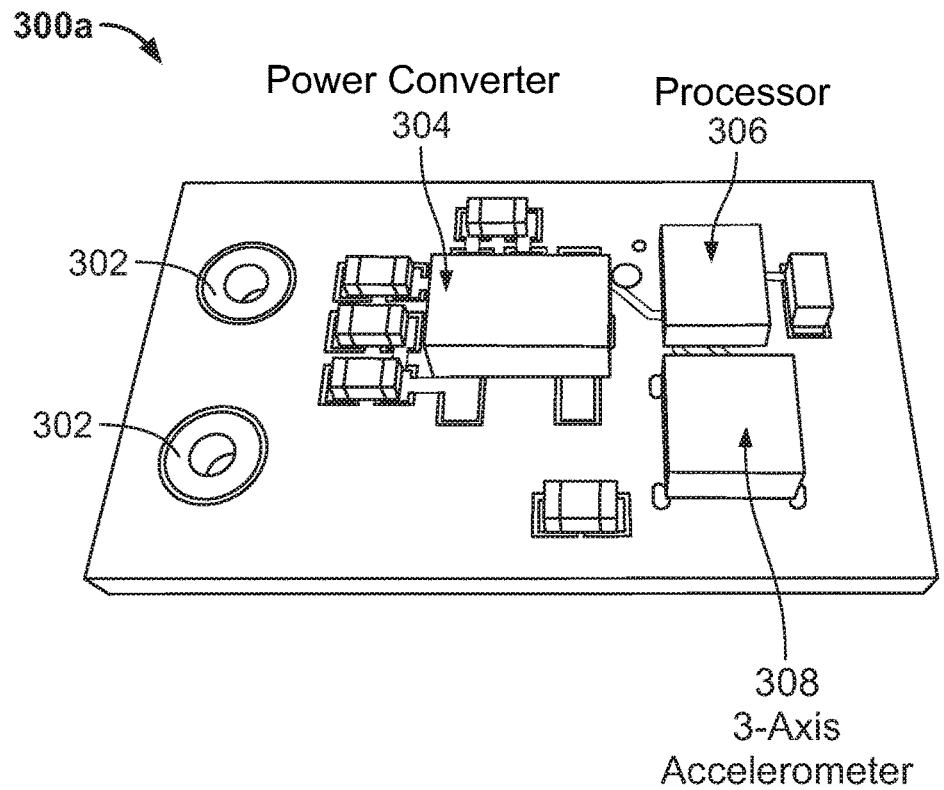
FIG. 3A illustrates a first portion of a PCB configured to carry components of motion sensor system shown in FIG. 2, in accordance with some embodiments of the present specification.
Figure 3B:
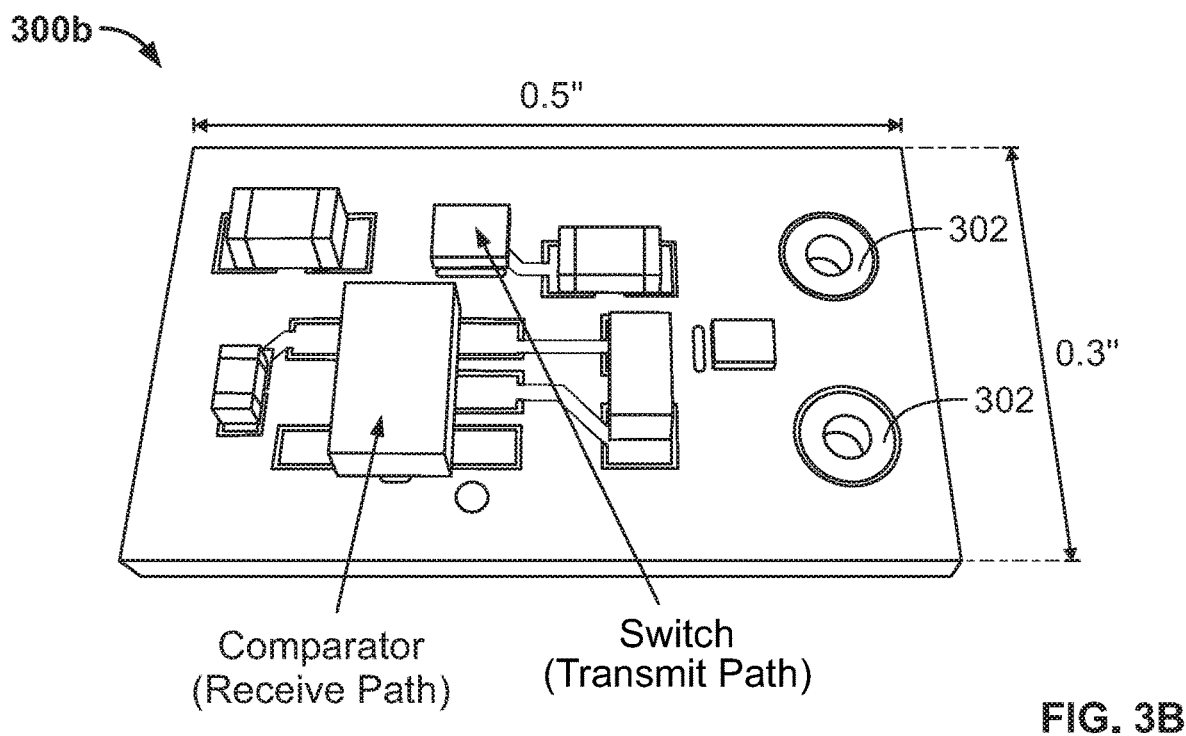
FIG. 3B illustrates a second portion of a PCB, which is on a side opposite to the side of first portion, configured to carry components of motion sensor system shown in FIG. 2, in accordance with some embodiments of the present specification.

FIG. 3A illustrates a first portion 300a of a PCB configured to carry components of motion sensor system 204 shown in FIG. 2, in accordance with some embodiments of the present specification. FIG. 3B illustrates a second portion 300b of a PCB, which is on a side opposite to the side of first portion 300a, configured to carry components of motion sensor system 204 shown in FIG. 2, in accordance with some embodiments of the present specification. Referring simultaneously to FIGS. 3A and 3B, the PCB (300a, 300b) is configured to be housed within a housing of a receptacle of a lead connecting wire that couples the motion sensor system to a monitoring device that stores and processes motion sensor data alone, or in combination with other physiological monitoring data. In embodiments, the PCB (300a, 300b) is sized in order to fit within the housing of the receptacle. In one embodiment, the PCB (300a, 300b) is 0.5 inches long and 0.3 inches wide, with electrical and electronic components on both sides. In some embodiments, electrical pads 302 on the PCB (300a, 300b) are configured to solder the ground and power/communication wires to the PCB (300a, 300b).

The connecting wire may be soldered to one of the electrical pads 302 to enable communication between PCB (300a, 300b) components and a power source and physiological data monitoring device. Power from the source may be communicated over the connecting wire and received by a power converter 304. Power converter 304 is configured to drop the power on the cable down to a recommended chip voltage and to remove the fluctuation of the power due to the signalling, and thereby power the electronic components of PCB (300a, 300b). A processor 306 is configured to both process sensor data and facilitate communication to and from the physiological monitoring device. A motion sensor 308 detects position and movement-related data and provides the data to processor 306. In some embodiments, motion sensor 308 is a multi-axis accelerometer. In one embodiment, motion sensor 308 is a tri-axis accelerometer. In various embodiments, motion sensor 308 could include a '6-axis' sensor (3-axis accelerometer and 3-axis gyroscope), or a '9-axis' sensor (3-axis accelerometer, 3-axis gyroscope, and 3-axis magnetometer). The sensors are used to provide positional and orientation information in 3-axis, which could be used to determine an orientation of a patient, such as determining if a patient is facing down a corridor as opposed to across it. Given that an accelerometer will indicate a value of 1 G straight downward (due to gravity), the accelerometer may be used to determine inclination of a patient. Quick changes in the acceleration indicated by the accelerometer may show motion of the subject, whereas slow changes in the acceleration may indicate an inclination change (for example, sitting up or rolling on one's side). Motion sensor 308 is configured to detect at least one or more of a position, inclination, and movement of the subject.

Embodiments of the present specification can be configured to interface with different types of physiological monitoring devices, such as respiration monitoring devices, BP monitoring devices, and devices that monitor multiple physiological parameters but, in each case, are preferably positioned within the housing of a conventional physiological sensor positioned on the patient's body.

Embodiments of the present specification are used to monitor exercise data of the subject. Activity levels may be quantified to provide helpful indications about the exercises performed by the subject. For example, the number of steps can be monitored. Embodiments of the present specification may also be used to indicate a type and duration of one or more activities performed by the subject. For example, physiological data is combined with posture information to determine whether the subject is sitting, standing, awake, or asleep, for a healthy duration. Similarly, embodiments may be used to determine levels of inactivity. For example, a subject who is bed-ridden is monitored for duration(s) of inactivity and an alarm is generated to remind that the subject needs to be moved to avoid bed-sores, or if they have deceased. Embodiments can be used to also detect fall of a subject. Embodiments can also be used to detect movement by a subject that may be unwarranted, accidental, or unhealthy. For example, movement of a subject exiting the bed can be detected when they are not supposed to leave on their own. Embodiments can also be used to detect rapid movements, such as but not limited to seizures, tremors, epileptic episodes, shivers, rapid breathing due to discomfort, coughing, vomiting, and rolling in bed.

Embodiments of the present specification may combine respiration detection data with motion sensor data to monitor chest motion and detect apnea. Additionally, measurement of respiration characteristics can be suppressed during a healthy exercise regimen. Similarly, when combining BP measurement data, a monitoring attempt can be cancelled, delayed or retried at later time, if the subject is identified to be excessively active.

Embodiments of the present specification assist in minimizing false ECG ST Segment alarms, which may otherwise occur due to positional changes. Additionally, false ECG rhythm alarms, such as v-tach (ventricular tachycardia), v-run (ventricular run), or any other ECG parameter, due to changes in position or due to motion, are minimized. A combination of ECG data, respiration data, BP data, with the motion sensor data in accordance with the embodiments of the present specification can detect and raise an appropriate alarm if a subject has a critical condition, for example, if the heart rate is low and there is a decrease in pulse amplitude.

Figure 4:
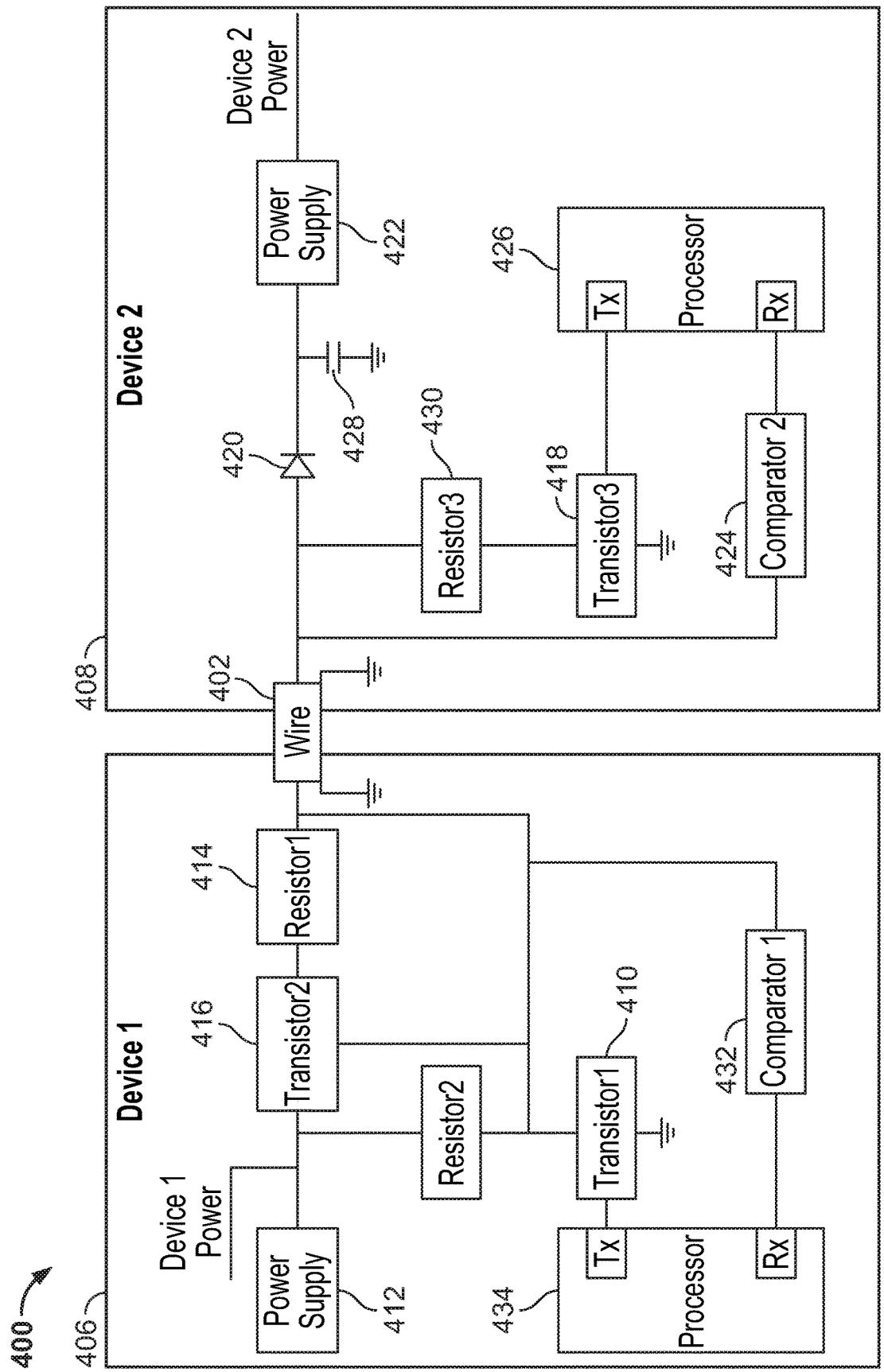
FIG. 4 is a block diagram illustrating components of two devices that share power and communication over a single wire, in accordance with some embodiments of the present specification.

Referring now to FIG. 4, a block diagram 400 of two devices that are connected using a single wire 402 for power and data communication is illustrated in accordance with some embodiments of the present specification. In embodiments, device 406 corresponds to device 110 (FIG. 1A) used for physiological monitoring, and device 408 corresponds to an integrated motion sensor system 204 (FIG. 2) placed within a receptacle 106 (FIG. 1A). In embodiments, a first device 406 and a second device 408, are respectively configured as a master device and a slave device. Device 406 provides power to device 408, and both devices communicate with each other over wire 402. In some embodiments, multiple slave devices are connected to first device 406.

In one embodiment during normal operation, a first transistor 410 in first device 406 does not conduct, thus allowing power from a power source and through a power module 412, through a second transistor 416, and through a first resistor 414 to wire 402 and thus to any connected devices, such as device 408. First device 406 and second device 408, each have a transistor 416 and 418, respectively, which are non-conducting. The transistor 418 in second device 408 is normally non-conducting. Therefore, the power sourced by device 406 over wire 402 to device 408 flows through a diode 420 positioned between transistor 418 and a power module 422 within device 408, towards power module 422. A comparator 424 is configured to receive power sent over wire 402, within device 408. Comparator 424 compares the input power rail to a reference voltage and outputs a low' to a receiving pin on a processor 426 of device 408.

In one embodiment, for transmitting a bit from first/master device 406 to second/slave device 408, first transistor 410 is moved to a conducting state which switches transistor 416 to a non-conducting state. The side of first resistor 414 that is connected to wire 402, is pulled low' through conducting transistor 410. On the other side of wire 402, in second device 408, comparator 424 senses the input supply going low' and switches the receiving pin on processor 426 to 'high'. In some embodiments, low' and 'high' signify a level of voltage, which can be interpreted by digital circuits as binary data. In some embodiments the 'high' and low' states can be opposite—that is what is specified in this description as a low' could be a 'high' and a 'high' could be a 'low'. In some embodiments, the transition on the receiving pin, from low' to 'high' denotes a binary '1'. Diode 420 prevents the voltage into the power module 422 of second device 408 from dropping rapidly. A capacitor 428 positioned between the line connecting resistor 420 and power module 422, and the ground, provides a small amount of power as the power supplied to device 408 through its power module 422 starts to drain the current from that node. The combination of diode 420 and capacitor 428 momentarily minimizes the voltage drop into the power supply from power module 422.

Once a sufficient amount of time is given for second device 408 to have seen the input from wire 402 drop 'low', first device 406 turns first transistor 410 back to a non-conducting state, which turns transistors 416 to a conducting state, thereby allowing a normal amount of current to flow through wire 402. If first transistor 410 is turned on to a conducting state and then back to a non-conducting state relatively quickly, second device 408 registers the change as data, but the power supplied to second device 408 remains constant. The amount of time in which transistor 410 changes its state from on to off may be determined on the basis of amount of current consumed by device(s) 408, the leakage of current back through diode 420, and the size of capacitor 428.

For second device 408 to transmit a bit of data to first device 406, transistor 416 and therefore transistor 418 are turned on to a conducting state by processor 426. Input from wire 402 through a resistor 430, positioned between output of wire 402 and transistor 418 of second device 408, is momentarily pulled 'low'. A comparator 432 on first device 406 senses the power output through resistor 414 drops to 'low' and consequently changes a receiving pin on a processor 434 within first device 406 to 'high'. After a sufficient amount of time expires, processor 426 on second device 408 switches off conduction through transistor 418 and wire 402 input to second device 408 rapidly rises back up to the supply level since that input is no longer shorted to ground. Comparator 432 detects the output voltage transitioning back to 'high' and sets the receiving pin on processor 434 of first device 406 back to 'low'.

In embodiments, resistor 414 on first device 406 keeps the regulator of first device 406 (the supply) from overcurrent during the intermittent short circuit events seen on the power line during transmission by second device 408. During these transmissions, transistors 416 and 410 are in a conducting state, so any momentary short circuit events of wire 402 are detected by power module 412 which puts system 400 into an overcurrent condition.

The communication over wire 402 is asynchronous, implying that a device (first device 406 or second device 408) could initiate communication on wire 402 at any time. Therefore, it is important for each device 406 and 408 to be able to detect possible data collisions. A data collision may occur when both devices 406 and 408 are sending data at the same time. When a device wishes to transmit data, it enters into a transmit state. In that state it should only detect the receiving pin change state when it has changed the state of a device processor's transmitting pin. If the receiving pin changes when the transmitting pin has not changed, then the processor (434, 426) concludes that it has sensed a collision and an upper level protocol of processors 434 and 426 of system 400 are signaled of such an event. It will be up to the upper level protocol to initiate any corrective action (usually a backoff for some random amount of time followed by a retry).

Figure 5:
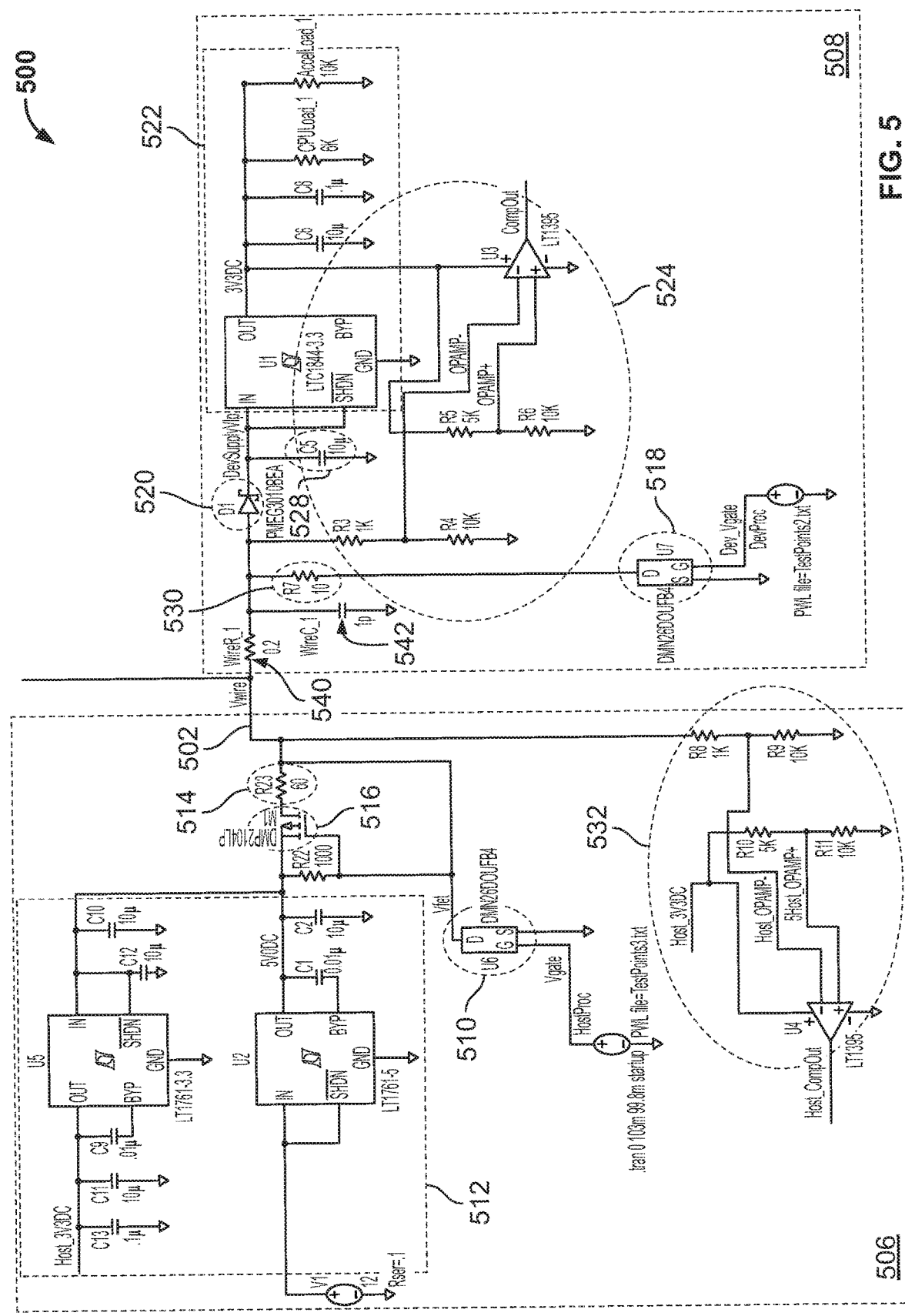
FIG. 5 is an exemplary simulation circuit that implements single wire communication in accordance with some embodiments of the present specification.

FIG. 5 illustrates an exemplary circuit 500 where the systems in accordance with some embodiments of the present specification were simulated. In one embodiment, a left side of the circuit 500 relates to a device 506 corresponding to first device 406 described with reference to FIG. 4. Similarly, a right side of circuit 500 relates to a device 508 corresponding to second device 408 of FIG. 4. A wire 502 (402) connects devices 506 (406) and 508 (408). Components of FIG. 5 correspond to the various components of FIG. 4 and are numbered similarly. For example, transistors 510 and 516 correspond to the transistors 410 and 416 of first device 406/506. In alternative embodiments, there can be multiple devices similar to device 508, which may be connected to device 506 through wire 502. In embodiments, the number of devices, similar to device 508, which may be connected through wire 502 to device 506, is limited by the power supplied by device 506 and consumed by multiple devices 508. Additionally, the numbers of multiple device 508 is limited by the protocols' ability to address more than a specific number of devices individually. In one embodiment, up to eight devices 508 are connected to device 506.

Referring again to FIG. 4, a voltage supply simulation 'HostProc' which is connected to $V_{gate}$ simulates the interaction with processor 434. The remaining portions of processor 434 are not simulated. Similarly, a voltage supply simulation 'DevProc' simulates the interaction of the processor 426 and the remaining portions of that processor are not simulated. Referring to FIG. 5, a resistance 'WIreR_1' 540 and capacitance 'WireC_1' 542 are used to simulate parasitic resistances and capacitances of the wire 502. Finally, component U5 and associated components C9 through C13, in the power supply 512 of the first device 506, are optional. In some embodiments voltage dividers and op-amps make up comparator portions 524 and 532, respectively within devices 508 and 506, of circuit 500. However, there is no restriction to that portion of the circuit—other circuits such as those with internal references may also be used.

Figure 6A:
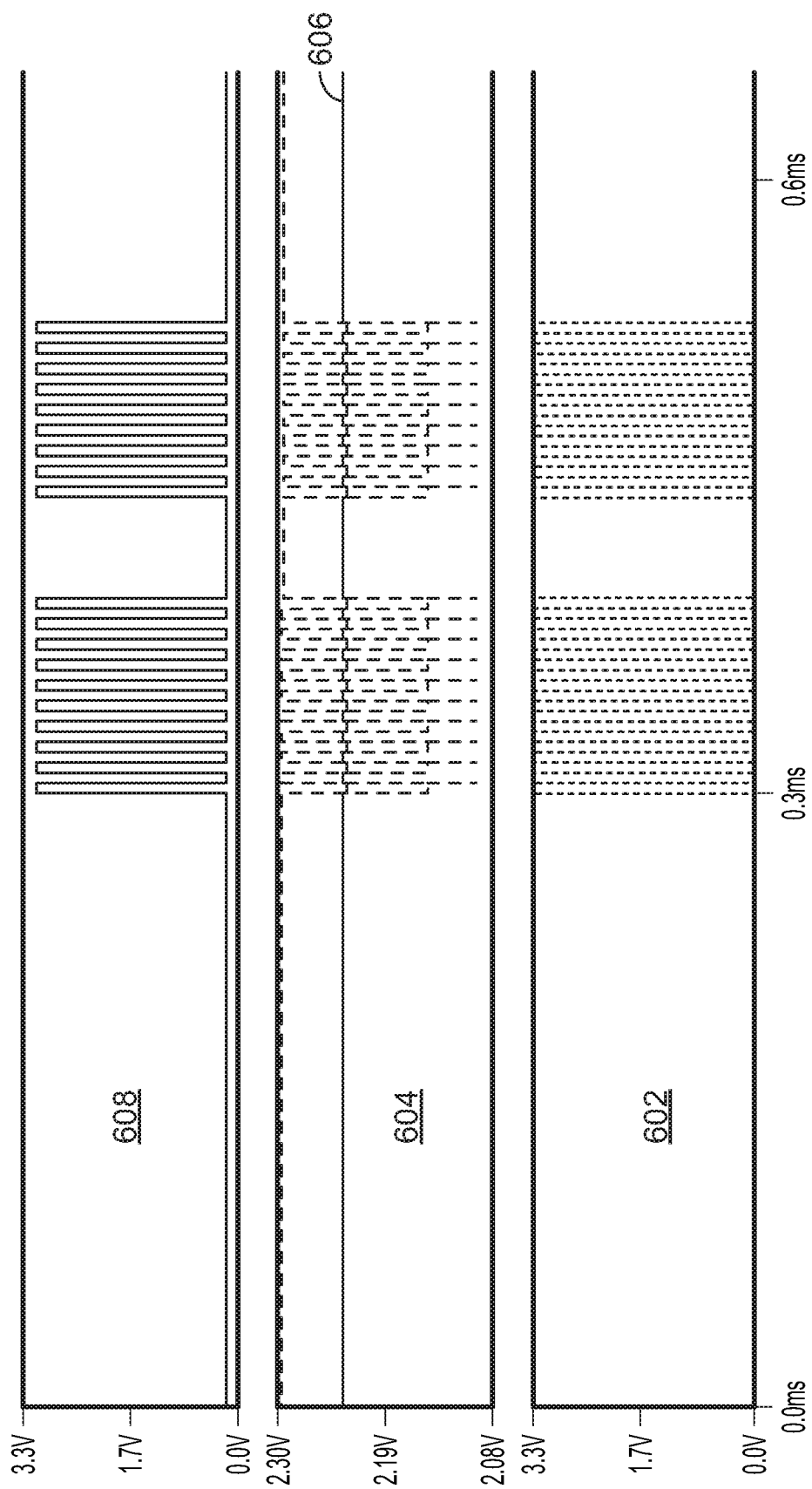
FIG. 6A illustrates a sample of data transmission from a first device to a second device using the simulation circuit of FIG. 5, in accordance with some embodiments of the present specification.

FIG. 6A illustrates transmission of data from first device 406/506 to second device 408/508, shown in FIGS. 4 and 5, in accordance with some embodiments of the present specification. Simultaneous reference to components of FIGS. 4 and 5 is made to enhance the description of the graphs. The figure shows transmission of a value of 0xFFFF (2 sets of 8 bits of 1's). Lower graph 602 shows the input provided to the transmit transistor (transmitting pin of transistor 410 of FIG.

4). Middle graph 604 shows comparator 424/524 op-amp inputs on second device 408/508 where a line 606 drawn across graph 604, is the reference voltage. In an embodiment, the reference voltage is between 2.19V and 2.3V. Top graph 608 shows the output of comparator 42/524 which is for all practical purposes identical to the transmitted input. In an exemplary embodiment, these transmissions were simulated at a rate of 100 KHz.

FIG. 6B illustrates transmission of data from second device 408/508 to first device 406/506 in response to the data transmission of FIG. 6A, in accordance with some embodiments of the present specification. In a first graph 632, a top trace 634 shows the input supply rail to the regulator 422 of second device 408/508. Some amount of expected sag is seen in trace 632, which occurs as a result of the power input intermittently dropping out. The output of that supply, however, remains constant at 3.3V (as shown in a lower trace 636 of graph 632) since the input is above the drop-out limit of the regulator. In some embodiments, regulators with low dropout values are selected to keep the slave device(s), such as second device 408/508, from drawing the power down below into the dropout range of their regulator(s). Alternatively, in some embodiments, the power resistor, such as resistor 414, is adjusted. A second graph 630 shows the current through resistor 414. A graph 628 below graph 630 shows comparator 432 output of first device 406/506, which is identical to the inputs from both of devices 406/506 and 408/508. A fourth graph 622 shows op-amp inputs 624 of first device 406/506 with a straight line 626 being the reference input voltage. A graph 618 shows an output 620 of the comparator 424. Traces 614 in a graph 616 show the signal and reference inputs, respectively, to the comparator 424. A trace 610 in a lower graph 612 is the input to transistor 418 of second device 408/508.

Additionally care needs to be taken to minimize the pulse widths of the bits transmitted and to allow enough recovery time in-between transmissions. Therefore, the pulse width of each bit is controlled. The bandwidth (baud rate) at which the transmission is driven may be a factor in controlling the pulse width for each bit. Independent of the baud rate, if the actual data transmission rate is low, a sag in the applied voltage is small. As the transmission rate increases and approaches the full bandwidth (baud rate) of the channel, the sag will worsen. In some embodiments, these signals are in the kHz range and the low portion of the pulse is minimized. In embodiments, pulse width depends upon the speed of each processor (434 and 426) and on the current draw of each 408 device. The size of capacitor 428, the leakage of diode 420, and the drop-out voltage value of regulator 422 may also affect the pulse width. Pulses of equal high and low widths that are between 1 kHz and 100 kHz are easily accommodated without resorting to larger or more expensive components.

Figure 7C:
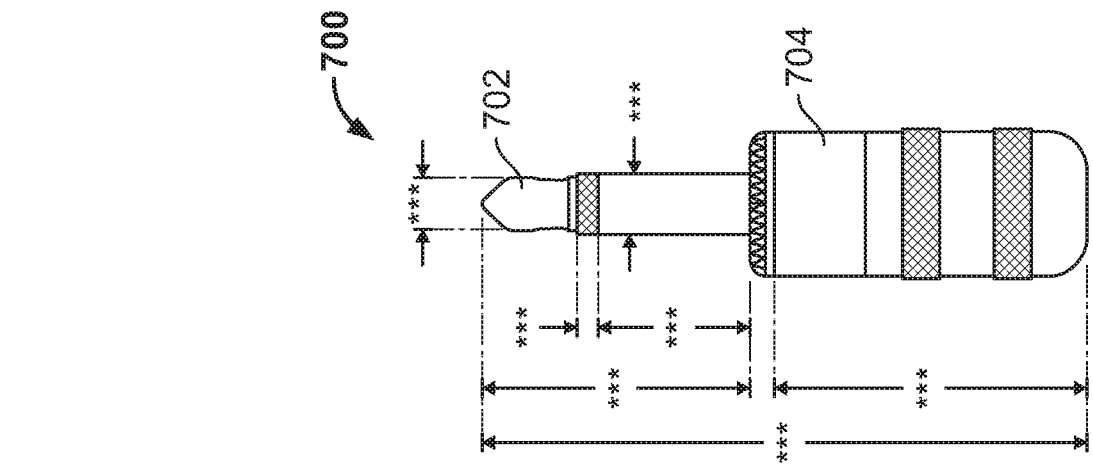
FIG. 7C is a schematic drawing of the plug portion of the wire, shown in FIG. 7A, along with dimensions of its components.
Figure 7A:
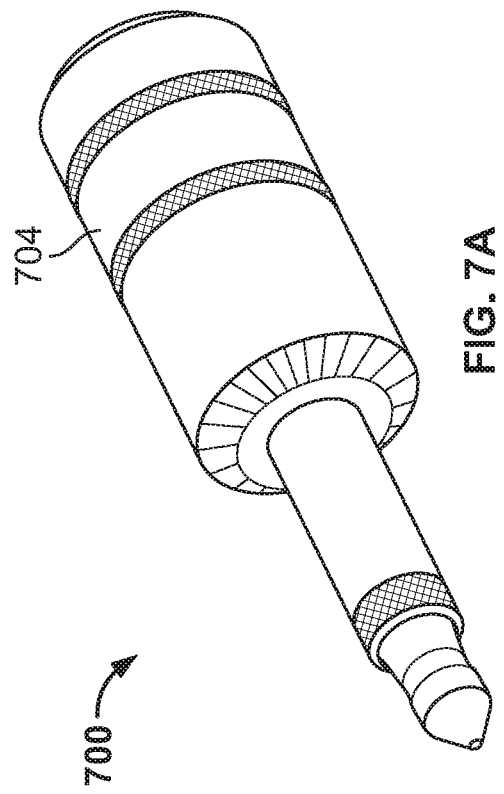
FIG. 7A is a photograph of a plug portion of a wire, in accordance with some embodiments of the present specification.
Figure 7B:
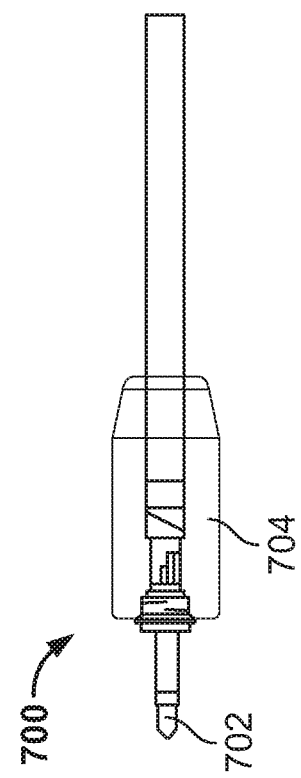
FIG. 7B is a line drawing of the plug portion of the wire shown in FIG. 7A, including a cross-sectional view of its housing.

FIGS. 7A, 7B, and 7C illustrate images of a first end 700 of a wire that connects the first master device 406 (FIG. 4) and the second slave device 408 (FIG. 4), in accordance with some embodiments of the present specification. The first end 700 is a plug portion of the wire that connects with a physiological monitoring system, such as device 110 shown in FIG. 1. FIG. 7A illustrates a photograph of the plug portion 700, in accordance with some embodiments of the present specification. FIG. 7B illustrates a line drawing of the plug portion 700, including a cross-section view of its housing. FIG. 7C illustrates a line drawing of the plug portion 700 with dimensions of its components. Referring simultaneously to FIGS. 7A, 7B, and 7C, the plug portion comprises a pin 702 that is configured to be placed inside a corresponding female port of the physiological monitoring device, thereby providing an electrical connection between the wire and the physiological monitoring device. A pointed end of the pin 702, extending for a length of approximately 3.9 millimeters (mm) and with a diameter of approximately 2.35 mm, emerges from a band of approximately 0.8 mm that joins the pointed end of the pin 702 to an opposite end of the pin 702, which extends for a length of approximately 6.7 mm and has a diameter of approximately 2.46 mm. At the opposite end, the pin 702 is connected to a protective housing 704. The housing 704 encompasses a switch with electrical components of the wire that provides communication of power and data from and to the physiological monitoring device when the pin is plugged into the physiological monitoring device. A total length of the plug portion 700 extends for approximately 25.9 mm. In embodiments, the pin portion 700 plugs into a special pin on the physiological monitoring device or is built into a yoke.

FIGS. 8A to 8D illustrate different views of a wire 800 with a plug portion 802 at one end and a receptacle portion 804 at the other end, in accordance with some embodiments of the present specification. FIG. 8A illustrates a top view of the receptacle portion 804 of the wire 800. FIG. 8B illustrates a side view of the receptacle portion 804 of the wire 800. FIG. 8C illustrates a cross-sectional side view of the receptacle portion 804 of the wire 800. FIG. 8D illustrates a bottom view of the receptacle portion 804 of the wire 800. In some embodiments, the wire 800 comprises a coaxial cable so as to avoid crosstalk. In different embodiments, the length of the wire 800 is different to suit various applications. For ECG applications, the length of wire 800 is similar to an ECG lead wire. Similarly, for ECG applications, wire 800 has a bend radius that is similar to the bend radius of an ECG lead wire. In embodiments, the wire 800 is applied and removed using its plug portion 802 using a similar force and technique for plugging and removing ECG lead wires. The receptacle portion 804 corresponds to the receptacle 200 of FIG. 2, which includes a housing 806 that encompasses components of an integrated motion sensor system. A lead connector is located at a one end of the connecting wire 800 within a portion of the housing 806 that interfaces with an electrode connector, analogous to an ECG electrode connector for the purpose of attaching receptacle portion 804 to the body of a patient. The motion sensor system, as described above, may comprise multiple components placed on a printed circuit board (PCB), and including elements that detect and process position and movement-related data. In embodiments, the housing 806 is watertight. The receptacle portion 804 may be configured as any of the known and used connectors to position on a subject.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A sensor configured to monitor a motion of a person and to monitor a physiological parameter of the person, wherein the sensor is configured to communicate with a monitoring system and wherein the monitoring system is at least one of an electrocardiogram (ECG) monitoring device, a respiration monitoring device, a SpO2 monitoring device, or a blood pressure monitoring device, the sensor comprising:
- a lead wire comprising
  - a connecting wire having a first end and an opposing second end;
  - a connector plug attached to the first end, wherein the connector plug is configured to electrically connect the lead wire with said monitoring system;
  - a receptacle at the second end, wherein the receptacle is configured to attach to the person;
  - a first printed circuit board integrated into the receptacle comprising a motion detector, wherein the motion detector is configured to acquire positional and movement information of the person and transmit the positional and movement information over the connecting wire, wherein the first printed circuit board is configured as a slave to a master printed circuit board located in the monitoring system, wherein the master printed circuit board comprises a power source and physiological sensor configured to acquire physiological data of the person, wherein the physiological data comprises at least one of ECG data, respiration data, SpO$_2$ data, or blood pressure data, wherein the first printed circuit board is configured to receive power from the master printed circuit board and compare said received power to a reference, and wherein the physiological sensor and motion detector are configured to communicate data asynchronously across the connecting wire.

2. The sensor of claim 1, further comprising a power converter on the first printed circuit board for receiving power from the power source at the first printed circuit board via the connecting wire.

3. The sensor of claim 1, further comprising an electrode configured to detect electrical signals generated by the person's cardiac activity.

4. The sensor of claim 3, wherein the electrode is partially exposed outside the receptacle.

5. The sensor of claim 3, wherein the electrode is configured to transmit the electrical signals generated by the person's cardiac activity through the connecting wire.

6. The sensor of claim 3, wherein the electrode is adapted to be positioned adjacent the motion detector and wherein the motion detector comprises at least one of a three-axis accelerometer, a combination of a three-axis accelerometer and a gyroscope, or a combination of a three-axis accelerometer, a gyroscope, and a magnetometer integrated therein.

7. The sensor of claim 1, wherein, when the second printed circuit board is in a transmission state, the second printed circuit board is configured to detect a change in a receiving state of the second printed circuit board, and adapted to halt transmission for a period of time based on said receiving state and wherein the period of time is a period of time of random length.

8. The sensor of claim 1, wherein, when the second printed circuit board is in a transmission state, the second printed circuit board is configured to detect a change in a receiving state of the second printed circuit board, and adapted to halt transmission for a period of time based on said receiving state and wherein, after said period of time has elapsed, the second printed circuit board is configured to reinitiate transmission.

9. An electrocardiogram monitoring system configured to monitor a motion of a person and to monitor electrical signals generated by the person's heart, comprising:
- a monitoring device configured to receive data indicative of the electrical signals and data indicative of the motion of the person, wherein the monitoring device comprises at least two ports;
- a first electrocardiogram lead wire having a first end with a connector configured to connect to either of the at least two ports and having a second end with a first receptacle, wherein the first receptacle is configured to attach to the person and wherein the first receptacle comprises an electrode and does not comprise a motion detector; and
- a second lead wire having a first end with a connector configured to connect to either of the at least two ports and having a second end with a second receptacle, wherein the second receptacle is configured to attach to the person, wherein the second receptacle comprises a first printed circuit board integrated into the second receptacle comprising a motion detector configured to acquire positional and movement information of the person and transmit the positional and movement information over the second lead; and
- a second printed circuit board integrated into the monitoring device comprising a physiological sensor and a power source, wherein the physiological sensor is configured to acquire physiological data of the person and transmit the physiological data over the first electrocardiogram lead wire, wherein the first printed circuit board is configured as a slave to the second printed circuit board, wherein the first printed circuit board and the second printed circuit board are connected via the second lead wire; wherein the first printed circuit board is configured to receive power from the second printed circuit board over the second lead wire and compare said received power to a reference, and wherein the physiological sensor, via the first electrocardiogram lead wire, and motion detector, via the second lead wire, are configured to asynchronously communicate data with the monitoring device.

10. The electrocardiogram monitoring system of claim 9, wherein the second lead wire is further adapted to channel power to the motion detector from the second printed circuit board and to transmit data to and from the motion detector.

11. The electrocardiogram monitoring system of claim 9, wherein, in the first electrocardiogram lead wire, the electrode is partially exposed through the first receptacle, is configured to detect the electrical signals, and is in electrical communication with the first electrocardiogram lead wire and wherein, in the second lead wire, the electrode is partially exposed through the second receptacle, is configured to detect the electrical signals, and is in electrical communication with the second lead wire.

12. The electrocardiogram monitoring system of claim 9, wherein, in the second lead wire, the electrode is positioned adjacent the motion detector and wherein the motion detector comprises at least one of a three-axis accelerometer, a combination of a three-axis accelerometer and a gyroscope, or a combination of a three-axis accelerometer, a gyroscope, and a magnetometer integrated therein.

13. The electrocardiogram monitoring system of claim 9, wherein the monitoring device comprises a third port.

14. The electrocardiogram monitoring system of claim 13, further comprising a third electrocardiogram lead wire having a first end with a connector configured to connect to either of the at least two ports or the third port and having a second end with a receptacle, wherein the receptacle is configured to attach to the person and wherein the receptacle comprises an electrode and does not comprise a motion detector.

15. The electrocardiogram monitoring system of claim 14, wherein the monitoring device comprises a fourth port.

16. The electrocardiogram monitoring system of claim 15, further comprising a fourth electrocardiogram lead wire having a first end with a connector configured to connect to either of the at least two ports, the third port or the fourth port and having a second end with a receptacle, wherein the receptacle is configured to attach to the person and wherein the receptacle comprises an electrode and does not comprise a motion detector.

17. The electrocardiogram monitoring system of claim 16, wherein each of the at least two ports, the third port and the fourth port are structurally equivalent and configured to receive a same shaped connector.

18. The electrocardiogram monitoring system of claim 9, wherein, when the second printed circuit board is in a transmission state, the second printed circuit board is configured to detect a change in a receiving state of the second printed circuit board, and adapted to halt transmission for a period of time based on said receiving state and wherein the period of time is a period of time of random length.

19. The electrocardiogram monitoring system of claim 9, wherein, when the second printed circuit board is in a transmission state, the second printed circuit board is configured to detect a change in a receiving state of the second printed circuit board, and adapted to halt transmission for a period of time based on said receiving state and wherein, after said period of time has elapsed, the second printed circuit board is configured to reinitiate transmission.

20. A method for monitoring a motion of a person and electrical signals generated by the person's heart, comprising:
   acquiring a monitoring device configured to receive data indicative of the electrical signals and data indicative of the motion of the person, wherein the monitoring device comprises at least two ports;
   connecting a first electrocardiogram lead wire to either of the at least two ports, wherein the first electrocardiogram lead wire comprises a first end with a connector configured to connect to either of the at least two ports and a second end with a first receptacle, wherein the first receptacle is configured to attach to the person and wherein the first receptacle comprises an electrode and does not comprise a motion detector;
   attaching the electrode of the first electrocardiogram lead wire to the person;
   connecting a second lead wire to either of the at least two ports, wherein the second lead wire has a first end with a connector configured to connect to either of the at least two ports and a second end with a second receptacle, wherein the second receptacle is configured to attach to the person, wherein the second receptacle comprises an electrode and a first printed circuit board comprising a motion detector configured to acquire positional and movement information of the person and transmit the positional and movement information over the second lead wire, wherein a second printed circuit board positioned in the monitoring device comprises a power source and a physiological sensor configured to acquire physiological data of the person, wherein the first printed circuit board is configured as a slave to the second printed circuit board, wherein the first printed circuit board and the second printed circuit board are connected via the second lead wire, wherein the first printed circuit board is configured to receive power from the second printed circuit board over the second lead wire and compare said received power to a reference, and wherein the motion detector is configured to asynchronously communicate data with the monitoring device;
   attaching the electrode of the second lead wire to the person;
   activating the monitoring device; and
   recording data indicative of the electrical signals and data indicative of the motion of the person.

21. The method of claim 20, wherein the second lead wire is further adapted to channel power from the second printed circuit board to the motion detector and to transmit data to and from the motion detector.

22. The method of claim 20, wherein, in the second lead wire, the electrode is positioned adjacent the motion detector having at least one of a three-axis accelerometer, a combination of a three-axis accelerometer and a gyroscope, or a combination of a three-axis accelerometer, a gyroscope, and a magnetometer integrated therein.

23. The method of claim 20, further comprising connecting a third electrocardiogram lead wire to either of the at least two ports or a third port, wherein the third electrocardiogram lead wire has a first end with a connector configured to connect to either of the at least two ports or the third port and a second end with a receptacle, wherein the receptacle is configured to attach to the person, wherein the receptacle comprises an electrode and does not comprise a motion detector and attaching the electrode of the third electrocardiogram lead wire to the person.

24. The method of claim 23, further comprising connecting a fourth electrocardiogram lead wire to either of the at least two ports, the third port, or a fourth port, wherein the fourth electrocardiogram lead wire has a first end with a connector configured to connect to either of the at least two ports, the third port or the fourth port, and a second end with a receptacle, wherein the receptacle is configured to attach to the person, wherein the receptacle comprises an electrode and does not comprise a motion detector and attaching the electrode of the fourth electrocardiogram lead wire to the person.

25. The method of claim 24, wherein each of the at least two ports, the third port and the fourth port are structurally equivalent and configured to receive a same shaped connector.

26. The method of claim 20, wherein, when the second printed circuit board is in a transmission state, the second printed circuit board is configured to detect a change in a receiving state of the second printed circuit board, and adapted to halt transmission for a period of time based on said receiving state and wherein the period of time is a period of time of random length.

27. The method of claim 20, wherein, when the second printed circuit board is in a transmission state, the second printed circuit board is configured to detect a change in a receiving state of the second printed circuit board, and adapted to halt transmission for a period of time based on said receiving state and wherein, after said period of time has elapsed, the second printed circuit board is configured to reinitiate transmission.

* * * * *